United States Patent
Peatfield et al.

(10) Patent No.: US 10,226,588 B2
(45) Date of Patent: *Mar. 12, 2019

(54) METHODS FOR DETECTING FAILURE STATES IN A MEDICINE DELIVERY DEVICE

(71) Applicant: Cequr SA, Horw (CH)

(72) Inventors: Gregory H. Peatfield, Atkinson, NH (US); Peter Gravesen, Nordborg (DK)

(73) Assignee: CEQUR SA, Horw (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/635,248

(22) Filed: Jun. 28, 2017

(65) Prior Publication Data

US 2017/0290997 A1 Oct. 12, 2017

Related U.S. Application Data

(63) Continuation of application No. 14/860,951, filed on Sep. 22, 2015, now Pat. No. 9,694,147, which is a
(Continued)

(51) Int. Cl.
*G08B 21/00* (2006.01)
*A61M 5/50* (2006.01)
(Continued)

(52) U.S. Cl.
CPC ............ *A61M 5/5086* (2013.01); *A61M 5/14* (2013.01); *A61M 5/1413* (2013.01);
(Continued)

(58) Field of Classification Search
CPC .. A61M 5/5086; A61M 5/16831; A61M 5/14; A61M 5/16886; A61M 5/14248;
(Continued)

(56) References Cited

U.S. PATENT DOCUMENTS 4,086,036 A 4/1978 Hagen et al.
4,237,775 A 12/1980 Eisele
(Continued)

FOREIGN PATENT DOCUMENTS

EP 0267041 A2 5/1988
EP 0450186 A1 10/1991
(Continued)

OTHER PUBLICATIONS

International Search Report and Written Opinion for PCT/US2010/044996, dated Jul. 20, 2011.

*Primary Examiner* — Anh V La
(74) *Attorney, Agent, or Firm* — Eversheds Sutherland (US) LLP

(57) ABSTRACT

A fluid medicament delivery device includes a patient attachment unit, containing the fluid medicament, and an indicator unit adapted to be detachably coupled to the patient attachment unit. A method for monitoring the fluid medicament includes independently setting a flow rate of a fluid medicament with the patient attachment unit. A pressure and/or a flow rate of the fluid medicament is sensed with a sensor located in a separate indicator unit in a sensing mode. A status of the fluid medicament delivery device is determined based at least in part on the pressure and/or the flow rate.

18 Claims, 22 Drawing Sheets

Related U.S. Application Data continuation of application No. 14/036,522, filed on Sep. 25, 2013, now Pat. No. 9,174,009, which is a continuation of application No. 12/542,954, filed on Aug. 18, 2009, now Pat. No. 8,547,239.

(51) Int. Cl.
  *A61M 5/14* (2006.01)
  *A61M 5/142* (2006.01)
  *A61M 5/168* (2006.01)

(52) U.S. Cl.
  CPC .... *A61M 5/14248* (2013.01); *A61M 5/16831* (2013.01); *A61M 5/16854* (2013.01); *A61M 5/16886* (2013.01); *A61M 2005/14252* (2013.01); *A61M 2005/14264* (2013.01); *A61M 2005/14268* (2013.01); *A61M 2005/16863* (2013.01); *A61M 2205/0244* (2013.01); *A61M 2205/18* (2013.01); *A61M 2205/3331* (2013.01); *A61M 2205/3334* (2013.01); *A61M 2205/3344* (2013.01); *A61M 2205/3358* (2013.01); *A61M 2205/50* (2013.01); *A61M 2205/581* (2013.01); *A61M 2205/582* (2013.01); *A61M 2205/583* (2013.01); *A61M 2205/587* (2013.01); *A61M 2205/70* (2013.01); *A61M 2207/00* (2013.01)

(58) Field of Classification Search
  CPC ............ A61M 5/16854; A61M 5/1413; A61M 2207/00; A61M 2205/587; A61M 2205/50; A61M 2005/16863; A61M 2205/581; A61M 2205/582; A61M 2205/3334; A61M 2205/3331; A61M 2205/18; A61M 2205/0244; A61M 2205/3358; A61M 2005/14268; A61M 2005/14264; A61M 2005/14252; A61M 2205/583; A61M 2205/70; A61M 2205/3344
  USPC ......... 340/603, 522, 573.1, 606; 604/65, 67, 604/506, 890.1
  See application file for complete search history.

(56) References Cited

U.S. PATENT DOCUMENTS

| | | |
|---|---|---|
| 4,435,173 A | 3/1984 | Siposs et al. |
| 4,443,218 A | 4/1984 | DeCant, Jr. et al. |
| 4,551,133 A | 11/1985 | Zegers de Beyl et al. |
| 4,617,014 A | 10/1986 | Cannon et al. |
| 4,715,852 A | 12/1987 | Reinicke et al. |
| 4,752,289 A | 6/1988 | Balding et al. |
| 4,755,173 A | 7/1988 | Konopka et al. |
| 4,756,706 A | 7/1988 | Kerns et al. |
| 4,784,577 A | 11/1988 | Ritson et al. |
| 4,784,645 A | 11/1988 | Fischell |
| 4,828,551 A | 5/1989 | Gertler et al. |
| 4,836,752 A | 6/1989 | Burkett |
| 4,898,579 A | 2/1990 | Groshong et al. |
| 4,920,972 A | 5/1990 | Frank et al. |
| 4,943,279 A | 7/1990 | Samiotes et al. |
| 4,994,035 A | 2/1991 | Mokros |
| 5,011,477 A | 4/1991 | Winchell et al. |
| 5,096,385 A | 3/1992 | Georgi et al. |
| 5,190,522 A | 3/1993 | Wojcicki et al. |
| 5,211,626 A | 5/1993 | Frank et al. |
| 5,257,980 A | 11/1993 | Van Antwerp et al. |
| 5,317,269 A | 5/1994 | Mills et al. |
| 5,321,392 A | 6/1994 | Skakoon et al. |
| 5,360,411 A | 11/1994 | Mimura et al. |
| 5,395,320 A | 3/1995 | Padda et al. |
| 5,492,533 A | 2/1996 | Kriesel |
| 5,522,799 A | 6/1996 | Furukawa |
| 5,524,907 A | 6/1996 | Walser |
| 5,625,151 A | 4/1997 | Yamaguchi |
| 5,681,284 A | 10/1997 | Herskowitz |
| 5,720,721 A | 2/1998 | Dumas et al. |
| 5,764,034 A | 6/1998 | Bowman et al. |
| 5,791,880 A | 8/1998 | Wilson |
| 5,839,467 A | 11/1998 | Saaski et al. |
| 5,843,014 A | 12/1998 | Lattin et al. |
| 5,851,197 A | 12/1998 | Marano et al. |
| 5,897,530 A | 4/1999 | Jackson |
| 5,899,218 A * | 5/1999 | Dugan ..................... F15C 5/00 137/1 |
| 5,928,194 A | 7/1999 | Maget |
| 5,984,894 A | 11/1999 | Poulsen et al. |
| 5,993,425 A | 11/1999 | Kriesel |
| 6,009,752 A | 1/2000 | Iwata |
| 6,126,637 A | 10/2000 | Kriesel et al. |
| 6,277,095 B1 | 8/2001 | Kriesel et al. |
| 6,293,925 B1 | 9/2001 | Safabash et al. |
| 6,358,225 B1 | 3/2002 | Butterfield |
| 6,416,291 B1 | 7/2002 | Butterfield et al. |
| 6,485,461 B1 | 11/2002 | Mason et al. |
| 6,520,938 B1 | 2/2003 | Funderburk et al. |
| 6,555,986 B2 | 4/2003 | Moberg |
| 6,585,707 B2 | 7/2003 | Cabiri et al. |
| 6,589,229 B1 | 7/2003 | Connelly et al. |
| 6,607,509 B2 | 8/2003 | Bobroff et al. |
| 6,647,860 B2 | 11/2003 | Savel et al. |
| 6,656,158 B2 | 12/2003 | Mahoney et al. |
| 6,656,159 B2 | 12/2003 | Flaherty |
| 6,659,980 B2 | 12/2003 | Moberg et al. |
| 6,669,669 B2 | 12/2003 | Flaherty et al. |
| 6,692,457 B2 | 2/2004 | Flaherty |
| 6,699,218 B2 | 3/2004 | Flaherty et al. |
| 6,723,072 B2 | 4/2004 | Flaherty et al. |
| 6,736,796 B2 | 5/2004 | Shekalim |
| 6,740,059 B2 | 5/2004 | Flaherty |
| 6,749,587 B2 | 6/2004 | Flaherty |
| 6,768,425 B2 | 7/2004 | Flaherty et al. |
| 6,830,558 B2 | 12/2004 | Flaherty et al. |
| 6,830,562 B2 | 12/2004 | Mogensen et al. |
| 6,852,094 B2 | 2/2005 | Beck et al. |
| 6,852,104 B2 | 2/2005 | Blomquist |
| 6,871,546 B2 | 3/2005 | Scheurich et al. |
| 6,892,755 B2 | 5/2005 | Black |
| 6,901,293 B2 | 5/2005 | Rogers et al. |
| 6,960,192 B1 | 11/2005 | Flaherty et al. |
| 6,997,907 B2 | 2/2006 | Safabash et al. |
| 7,000,806 B2 | 2/2006 | Py et al. |
| 7,018,360 B2 | 3/2006 | Flaherty et al. |
| 7,029,455 B2 | 4/2006 | Flaherty |
| 7,066,031 B2 | 6/2006 | Zdeblick et al. |
| 7,109,878 B2 | 9/2006 | Mann et al. |
| 7,137,964 B2 | 11/2006 | Flaherty |
| 7,144,384 B2 | 12/2006 | Gorman et al. |
| 7,207,974 B2 | 4/2007 | Safabash et al. |
| 7,291,126 B2 | 11/2007 | Shekalim |
| 7,303,549 B2 | 12/2007 | Flaherty et al. |
| 7,318,816 B2 | 1/2008 | Bobroff et al. |
| 7,341,572 B2 | 3/2008 | Bridle et al. |
| 7,377,907 B2 | 5/2008 | Shekalim |
| 7,544,185 B2 | 6/2009 | Bengtsson |
| 7,699,807 B2 | 4/2010 | Faust et al. |
| 7,713,258 B2 | 5/2010 | Adams et al. |
| 7,771,412 B2 | 8/2010 | Anderson et al. |
| 7,879,010 B2 | 2/2011 | Hunn et al. |
| 7,887,505 B2 | 2/2011 | Flaherty |
| 7,918,825 B2 | 4/2011 | O'Connor et al. |
| 7,935,104 B2 | 5/2011 | Yodfat et al. |
| 7,938,801 B2 | 5/2011 | Hawkins et al. |
| 7,976,500 B2 | 7/2011 | Adams et al. |
| 8,104,352 B2 | 1/2012 | Evering et al. |
| 8,162,892 B2 | 4/2012 | Mogensen et al. |
| 8,172,805 B2 | 5/2012 | Mogensen et al. |
| 8,202,250 B2 | 6/2012 | Stutz, Jr. |
| 8,246,581 B2 | 8/2012 | Adams et al. |
| 8,409,143 B2 | 4/2013 | Lanigan et al. |
| 8,547,239 B2 | 10/2013 | Peatfield et al. |

(56) References Cited

U.S. PATENT DOCUMENTS

| | | | |
|---|---|---|---|
| 8,613,724 B2 | 12/2013 | Lanier, Jr. et al. | |
| 8,628,498 B2 | 1/2014 | Safabash et al. | |
| 8,672,873 B2 | 3/2014 | Gravesen et al. | |
| 8,679,062 B2 | 3/2014 | Yodfat et al. | |
| 9,022,972 B2 * | 5/2015 | Gravesen | A61M 5/1413 604/505 |
| 2002/0087147 A1 | 7/2002 | Hooper et al. | |
| 2002/0161332 A1 | 10/2002 | Ramey | |
| 2002/0183693 A1 | 12/2002 | Peterson et al. | |
| 2003/0204274 A1 | 10/2003 | Ullestad et al. | |
| 2004/0026235 A1 | 2/2004 | Stowell | |
| 2004/0059316 A1 | 3/2004 | Smedegaard | |
| 2004/0133166 A1 | 7/2004 | Moberg et al. | |
| 2004/0158207 A1 | 8/2004 | Hunn et al. | |
| 2004/0167464 A1 | 8/2004 | Ireland et al. | |
| 2004/0204687 A1 | 10/2004 | Mogensen et al. | |
| 2004/0216103 A1 | 10/2004 | Burky et al. | |
| 2005/0043687 A1 | 2/2005 | Mogensen et al. | |
| 2005/0101932 A1 | 5/2005 | Cote et al. | |
| 2005/0109115 A1 | 5/2005 | Gatesman | |
| 2005/0124936 A1 | 6/2005 | Mogensen et al. | |
| 2005/0171512 A1 | 8/2005 | Flaherty | |
| 2005/0174216 A1 | 8/2005 | Lintell | |
| 2005/0182366 A1 | 8/2005 | Vogt et al. | |
| 2005/0203461 A1 | 9/2005 | Flaherty | |
| 2005/0238507 A1 | 10/2005 | Diianni et al. | |
| 2005/0266582 A1 | 12/2005 | Modlin et al. | |
| 2006/0030836 A1 | 2/2006 | Lee et al. | |
| 2006/0041229 A1 | 2/2006 | Garibotto et al. | |
| 2006/0161108 A1 | 7/2006 | Mogensen et al. | |
| 2006/0178633 A1 | 8/2006 | Garibotto et al. | |
| 2006/0184121 A1 | 8/2006 | Brcokman et al. | |
| 2006/0200073 A1 | 9/2006 | Radmer et al. | |
| 2006/0264835 A1 | 11/2006 | Nielsen et al. | |
| 2006/0282290 A1 | 12/2006 | Flaherty et al. | |
| 2007/0074722 A1 | 4/2007 | Giroux et al. | |
| 2007/0083153 A1 | 4/2007 | Haar | |
| 2007/0112301 A1 | 5/2007 | Preuthun et al. | |
| 2007/0118405 A1 | 5/2007 | Campbell et al. | |
| 2007/0156094 A1 | 7/2007 | Safabash et al. | |
| 2007/0231204 A1 | 10/2007 | Hyde et al. | |
| 2007/0250007 A1 | 10/2007 | Shekalim | |
| 2007/0282269 A1 | 12/2007 | Carter et al. | |
| 2007/0299397 A1 | 12/2007 | Alferness et al. | |
| 2008/0033361 A1 | 2/2008 | Evans et al. | |
| 2008/0051710 A1 | 2/2008 | Moberg et al. | |
| 2008/0051738 A1 | 2/2008 | Griffin | |
| 2008/0058718 A1 | 3/2008 | Adams et al. | |
| 2008/0086086 A1 | 4/2008 | Field et al. | |
| 2008/0116647 A1 | 5/2008 | Anderson et al. | |
| 2008/0119790 A1 | 5/2008 | Hawkins et al. | |
| 2008/0119822 A1 | 5/2008 | Knauper | |
| 2008/0139907 A1 | 6/2008 | Rao et al. | |
| 2008/0147044 A1 | 6/2008 | Palmer et al. | |
| 2008/0147050 A1 | 6/2008 | Mann et al. | |
| 2008/0160492 A1 | 7/2008 | Campbell et al. | |
| 2008/0172030 A1 | 7/2008 | Blomquist | |
| 2008/0183060 A1 | 7/2008 | Steil et al. | |
| 2008/0214919 A1 | 9/2008 | Harmon et al. | |
| 2008/0215006 A1 | 9/2008 | Thorkild | |
| 2008/0227210 A1 | 9/2008 | Smith | |
| 2008/0234630 A1 | 9/2008 | Iddan et al. | |
| 2008/0294094 A1 | 11/2008 | Mhatre et al. | |
| 2009/0012472 A1 | 1/2009 | Ahm et al. | |
| 2009/0012479 A1 | 1/2009 | Moller et al. | |
| 2009/0069749 A1 | 3/2009 | Miller et al. | |
| 2009/0099521 A1 | 4/2009 | Gravesen et al. | |
| 2009/0143732 A1 | 6/2009 | O'Connor et al. | |
| 2009/0192471 A1 | 7/2009 | Carter et al. | |
| 2009/0204077 A1 | 8/2009 | Hasted et al. | |
| 2009/0281497 A1 | 11/2009 | Kamen et al. | |
| 2010/0017141 A1 | 1/2010 | Campbell et al. | |
| 2010/0082011 A1 | 4/2010 | Lewis et al. | |
| 2011/0034883 A1 | 2/2011 | Gyrn et al. | |
| 2011/0043357 A1 | 2/2011 | Peatfield et al. | |
| 2011/0046558 A1 | 2/2011 | Gravesen et al. | |
| 2011/0056301 A1 | 3/2011 | Winkler et al. | |
| 2011/0098652 A1 | 4/2011 | Hasted et al. | |

FOREIGN PATENT DOCUMENTS

| | | |
|---|---|---|
| EP | 1177802 A1 | 2/2002 |
| EP | 1792655 A1 | 6/2007 |
| EP | 2029200 A2 | 3/2009 |
| EP | 2252349 A1 | 11/2010 |
| EP | 2349400 A2 | 8/2011 |
| EP | 2452709 A2 | 5/2012 |
| EP | 2531232 A2 | 12/2012 |
| EP | 2588160 A1 | 5/2013 |
| GB | 2031558 A | 4/1980 |
| WO | 1993/018305 A1 | 9/1993 |
| WO | 1994/027669 A1 | 12/1994 |
| WO | 1997/038322 A1 | 10/1997 |
| WO | 1999/001731 A1 | 1/1999 |
| WO | 2002/068015 A2 | 9/2002 |
| WO | 2002/070047 A1 | 9/2002 |
| WO | 2007/057038 A1 | 5/2007 |
| WO | 2008/017329 A1 | 2/2008 |
| WO | 2008/019898 A1 | 2/2008 |
| WO | 2008/020447 A1 | 2/2008 |
| WO | 2008/024810 A2 | 2/2008 |
| WO | 2008/078318 A2 | 7/2008 |
| WO | 2008/086007 A1 | 7/2008 |
| WO | 2009/016637 A2 | 2/2009 |

* cited by examiner

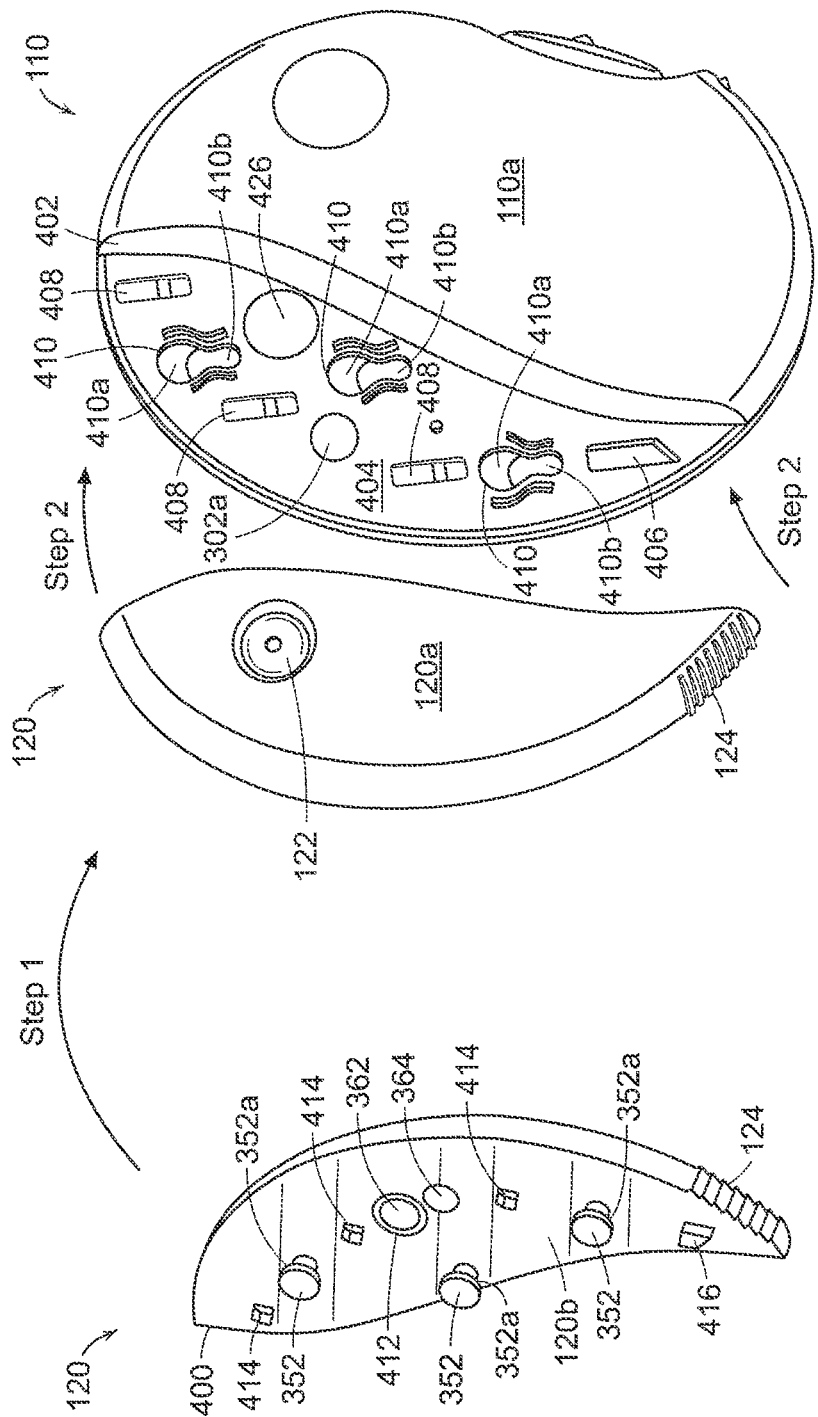

METHODS FOR DETECTING FAILURE STATES IN A MEDICINE DELIVERY DEVICE

CROSS-REFERENCE TO RELATED APPLICATIONS

This application is a continuation of U.S. patent application Ser. No. 14/860,951, filed Sept. 22, 2015, which is a continuation of U.S. patent application Ser. No. 14/036,522, filed Sept. 25, 2013, which is a continuation of U.S. patent application Ser. No. 12/542,954, filed Aug. 18, 2009, which are all hereby incorporated herein by reference in their entireties.

FIELD OF THE INVENTION

This invention relates generally to medicament delivery devices and, more specifically, to medicament infusion devices that utilize a reusable indicator unit and a disposable medicament delivery unit.

BACKGROUND

Medicament infusion devices are utilized to deliver liquid fluid medicine to patients. For example, insulin infusion devices are often used by persons with diabetes to maintain adequate insulin levels throughout the day or to increase insulin levels during mealtime. These insulin infusion devices can replace the syringe-based injections common among those with diabetes.

Insulin infusion devices are available in several forms, and include several common components. Generally, an infusion device includes a housing that may be worn on a patient's clothing (a belt, for example) or on the patient himself, and that contains a number of mechanical and electrical components. A reservoir holds the insulin and an electro-mechanical pump mechanism (various types are used) delivers the insulin as needed to the patient. Battery-powered electronics control the pump and ensure that the device is operating properly. Various sensors communicate with the electronics and other components to detect occlusions, sound alarms, measure remaining insulin capacity, etc.

While these devices are useful, they do suffer from several shortcomings. First, the high expense of the devices makes them accessible to fewer people than the diabetic population members who may benefit from their use. Second, failure or malfunction of one component requires repair or replacement of the entire device, a costly scenario. For example, if the pump fails, often the entire unit (including the properly functioning—and expensive—electronics) must be replaced. Third, over time the device gets dirty due to repeated uses, which requires periodic cleaning and may cause a failure condition at a later date. Fourth, the complexity of the devices requires significant battery power to operate pumps, monitor sensors, and send alerts and notifications to a patient. Power and electronic requirements are often so significant as to excessively require large batteries, thus increasing the physical size and cost of the device.

SUMMARY OF THE INVENTION

What is needed, then, is a medicament infusion device that utilizes low-cost components, some of which may be replaced periodically after use, without having to dispose of other expensive, but operational, components in the device.

In general, in one aspect, embodiments of the invention feature a system for monitoring a fluid medicament delivery device that includes a patient attachment unit and an indicator unit. The patient attachment unit independently sets a flow rate of a fluid medicament contained therein. The indicator unit monitors a parameter of interest of the fluid medicament is adapted to be detachably coupled to the patient attachment unit, and includes a sensing module, a status determination module, and a notification module. The sensing module for receives a signal, indicating at least one of a pressure and a flow rate of the fluid medicament, from a sensor located in the patient attachment unit. The status determination module determines a status of the fluid medicament delivery device based at least in part on the received signal. The notification module notifies a patient of the status.

The patient attachment unit may be adapted to be attached to a skin surface of the patient, and the sensing module may include a MEMS sensor. An initialization module may perform a system initialization test (e.g., a battery status test). A result of the battery status test may be based at least in part on a volume of the fluid medicament and/or an amount time. Based on the result, the notification module may notify the patient.

The status may include a fault condition (e.g., an out-of-fluid condition and a time limit condition) based at least in part on a volume of the fluid medicament, a pressure of the fluid medicament, a flow rate of the fluid medicament, a hardware fault, and/or an amount of time. The status may include a system-OK condition, an occlusion condition, and/or a low-reservoir volume condition. The patient attachment unit may include a variable-volume chamber in which a fluid is at least partially contained. The variable-volume chamber unit may include a flexible member, and a movement of the flexible member may be sensed by the sensing module. The notification module may further include an alarm (e.g., an audible alarm, a visual alarm, and/or a tactile alarm).

In general, in another aspect, embodiments of the invention feature a method for monitoring a fluid medicament delivery device. The device includes a patient attachment unit (which includes a reservoir for receiving the fluid medicament therein) and an indicator unit (which is adapted to be detachably coupled to the patient attachment unit). A flow rate of a fluid medicament in independently set with a patient attachment unit. During a sensing mode, a pressure and/or a flow rate of the fluid medicament are sensed with a sensor located in a separate indicator unit. A status of the fluid medicament delivery device is determined based at least in part on a result the pressure and/or the flow rate. The patient is notified of the status.

The patient attachment unit may be adapted to be attached to a skin surface of the patient. The sensing mode may be initiated upon receipt of an interrupt request, which may be triggered by an expiration of a sample timer and/or an actuation of a button. An ambient air pressure may be sensed, and the ambient air pressure may be compared to the fluid pressure. Forensic data may be stored in a nonvolatile memory.

A system initialization test (e.g., a battery power test and/or detecting a hardware fault) may be conducted, and the patient may be notified in the event of low battery power. Notifying the patient (e.g., sending an audible notification comprising at least two tones) may include sending a discreet notification followed by an overt notification, and the overt notification may be cancelled base at least in part on a request from the patient.

In another aspect, the invention relates to a fluid medicament delivery device having a patient attachment unit that includes a housing and a fluid channel located therein, such that at least a portion of the fluid channel has a flexible member substantially coterminous with the housing. The fluid medicament delivery device includes a separate indicator unit adapted to be detachably coupled to the housing of the patient attachment unit. The indicator unit includes a first sending element for contacting the flexible member when the indicator unit is coupled to the housing, such that the first sensing element senses a flexure of the flexible member. In an embodiment of the foregoing aspect, the indicator unit also includes a second sending element for sending a pressure external to the housing. In another embodiment, the pressure external to the housing includes an ambient pressure.

In an embodiment of the above aspect, the first sensing element includes a pressure sensor. In another embodiment, the first sensing element also includes at least one of a fluid and a gel adapted to contact the flexible member, such that the flexure of the flexible member is transmitted by the at least one of the fluid and the gel to the pressure sensor. In yet another embodiment, the separate indicator unit defines a well for containing at least one of the liquid and the gel. In still another embodiment, the separate indicator unit includes a raised lip surrounding the well, such that the raised lip is disposed above a proximate portion of the separate indicator unit. In another embodiment, the raised lip is adapted to contact the housing of the patient attachment unit.

In another embodiment of the above aspect, the second sensing element includes a pressure sensor adapted to sense the pressure external to the housing, and at least one of a fluid and a gel adapted to transmit the pressure external to the housing to the pressure sensor. In an embodiment, the housing has a hermetically-sealed housing defining an interior space and including at least one substantially flexible housing portion. The substantially flexible housing portion is adapted for transmitting the pressure external to the housing to the interior space. In still another embodiment, the substantially flexible housing portion is located on a portion of the patient attachment unit facing the separate indicator unit and the second sensing element is located on a portion of the separate indicator unit facing the patient attachment unit, when the patient attachment unit is coupled to the separate indicator unit.

In yet another embodiment of the foregoing aspect, the patient attachment unit is adapted for adhesion to a skin surface of a patient. In an embodiment, the fluid medicament delivery device also includes a processor adapted for interpreting a signal from a pressure sensor, such that the signal is sent to the processor based at least in part of the flexure of the flexible member.

In another aspect, the invention relates to a method of monitoring pressure within a fluid channel of a fluid medicament delivery device, the method including measuring an actual pressure of a fluid within the fluid channel, comparing the actual pressure to a pressure range including a maximum pressure and a minimum pressure, and sending a notification when the actual pressure is outside of the pressure range. In an embodiment, the method also includes measuring a pressure external to fluid medicament delivery device.

In an embodiment of the above aspect, the method of monitoring pressure within a fluid channel of a fluid medicament delivery device also includes modifying the actual pressure base on the external pressure to obtain a corrected pressure, and comparing the corrected pressure to the pressure range. In another embodiment, the method also includes modifying the maximum pressure and a minimum pressure of the pressure range based on the external pressure to obtain a corrected pressure range, and comparing the corrected pressure range to the actual pressure. In still another embodiment, when the actual pressure exceeds the maximum pressure, the notification includes at least one of a downstream occlusion notification and a near-empty reservoir notification. In yet another embodiment, when the actual pressure is less than the minimum pressure, the notification includes at least one of an upstream occlusion notification and an empty reservoir notification.

In another aspect, the invention relates to a method of manufacturing a pressure sensing element, the method including securing a pressure sensor to a base, securing a template defining a well therein to the base, such that the pressure sensor is located in a bottom portion of the well. The method includes filling at least partially the well with a gel having a substantially liquid state, so the well includes a filled portion and an unfilled portion, and the filled portion and the unfilled portion are characterized by a presence or and absence of gel. The method includes solidifying the gel in the filled portion to a substantially gelled state, and filling the unfilled portion with a gel having a substantially liquid state.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations

BRIEF DESCRIPTION OF THE FIGURES

Other features and advantages of the present invention, as well as the invention itself, can be more fully understood from the following description of the various embodiments, when read together with the accompanying drawings, in which:

FIGS. 9A-9D depict a procedure for mounting the indicator unit to the patient attachment unit in accordance with one embodiment of the present invention;

DETAILED DESCRIPTION

Figure 1:
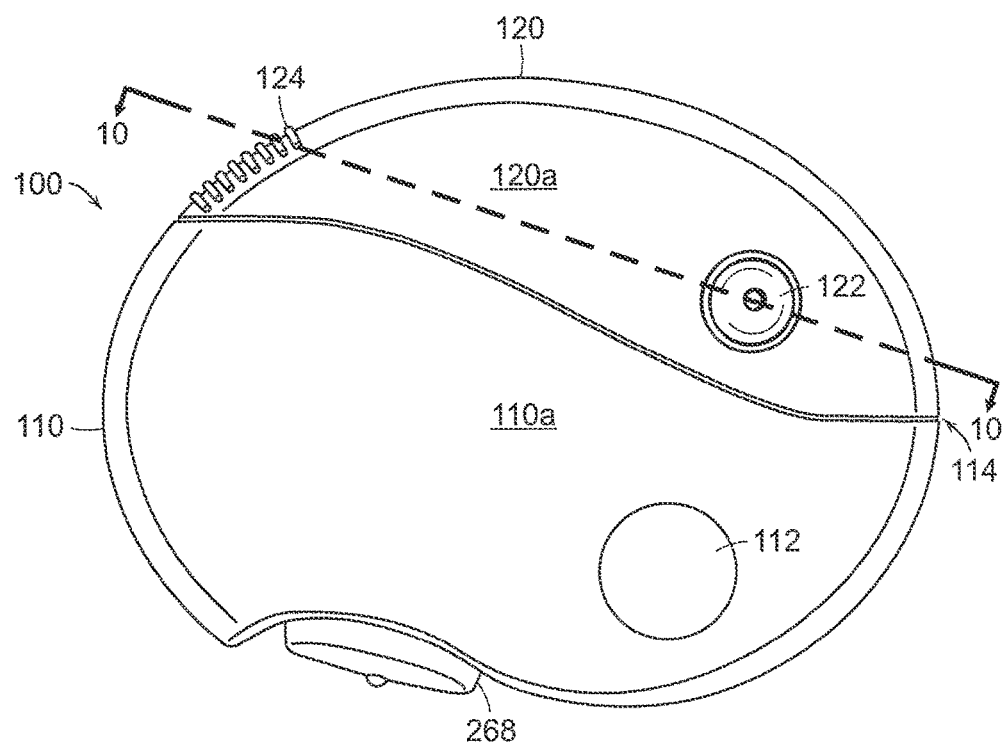
FIG. 1 is a schematic top view of a fluid medicament delivery device in accordance with one embodiment of the invention.
Figure 2:
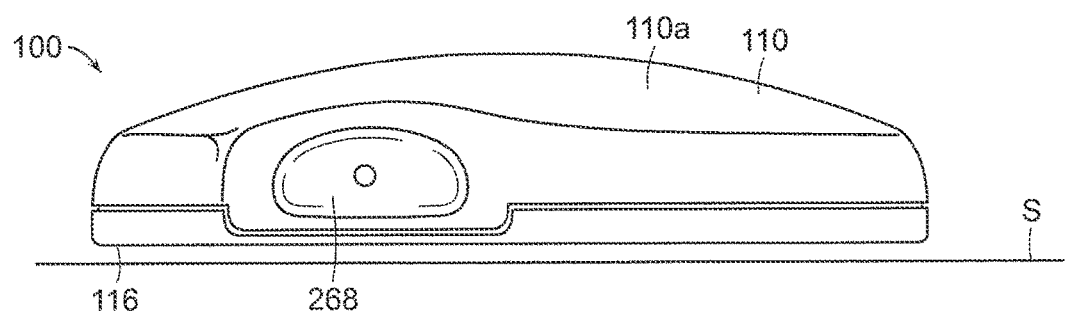
FIG. 2 is a schematic side view of the fluid medicament delivery device of FIG. 1.

FIGS. 1 and 2 depict an embodiment of an assembled fluid medicament delivery device 100 having at least tow modules, a patient attachment unit 110 and a separate indicator unit 120, each having a housing 110a, 120a, respectively. The depicted fluid medicament delivery device 100, when assembled, defines a substantially oval shape, although other shapes (circular, oblong, elliptical, etc.) are also contemplated. In general, an assembled device having round corners, smooth edges, etc., may be desirable, since the device is designed to be worn on the skin of a patient, underneath clothing. Other aspects of the device that make it generally unobtrusive during wear include a small size (only about several inches across) and a low profile. Other device shapes and sizes are also contemplated.

The patient attachment unit 110 includes a bolus button 268 for delivering a dose of fluid medicament, as described below. A cannula insertion device (See FIG. 13A) inserts a cannula through the device 110, subcutaneously through the skin S of a patient. Cannula insertion devices are described in U.S. patent application Ser. No. 12/250,760, filed Oct. 14, 2008, the disclosure of which is hereby incorporated by reference herein in its entirety. After insertion, the cannula insertion device is disconnected from the patient attachment unit 110, and a cap 112 is used to seal the opening to prevent ingress of contaminants, moisture, etc. The separate indicator unit 120 includes an indicator button 122. A textured edge 124, may be present on all or part of the edge of the housing 120a to provide a gripping surface during attachment and/or disconnection of the indicator unit 120 and the patient attachment unit 110, as described in more detail below. Alternatively or additionally, the edge of patient attachment unit housing 110a may also be textured.

The patient attachment unit 110 is connected to and in communication with the separate indicator unit 120, as described in more detail below. The housings 110a, 120b of the patient attachment unit 110 and the indicator unit 120 meet at a curved interface 114. Interfaces having other mating shapes are also contemplated. The bottom surface of the patient attachment unit 110 includes a patient attachment interface 116. The patient attachment interface 116 may include one or more adhesive pads secured to the bottom surface of the patient attachment unit 110 for adhering the fluid medicament delivery device 100 to the skin S of a patient during use. The interface 116 may comprise any suitable configuration to adhere the patient attachment unit 110 to the skin S. In one embodiment, the interface 116 includes a plurality of discrete points of attachment. Other embodiments utilize concentric adhesive circles or ovals.

the indicator button 122 may be used by the patient to test the functioning of the fluid medicament delivery device 100 or to cancel a notification presently being delivered or to prompt for a repetition of a previous message or other information stored by the indicator unit. Actuating the indicator button 122 may initiate one or more tests to indicate to the patient various operational or therapy states of the device 100, such as whether the separate indicator unit 120 is properly mounted to the patient attachment unit 110, whether an internal battery has sufficient power for continued use, and/or whether pressure sensing within the device 110 is operating properly. Other tests are also contemplated. A single indicator button, such as that depicted in FIG. 1, may be used to run one or more tests. The medicament delivery device 100 may be programmed to recognize patterns of actuations of the indicator button to initiate certain test routines. That is, two actuations in quick succession may initiate a "Battery Power Available" test routine, three actuations in quick succession may initiate a "Pressure Sensor Check" test routine, etc. Other combinations of short actuations and long actuations (e.g., Short, Long, Short, Long, Long, Short, etc.) are also contemplated to initiate any number of test routines. Alternatively or additionally, two or more buttons or other input features may be included on the device, for initiating one or more separate tests. Positive or negative feedback of the results may be provided to the patient in the form of audible sounds of differing tones or durations, illumination/delumination of lights, vibrations, and combinations thereof. In certain embodiments, light emitting diodes (LEDs) may be used to illuminate the button itself or may illuminate portions of the indicator unit housing to provide feedback to the patient. Graphical indicia or alphanumeric information may be displayed on a suitable output device.

Figure 3:
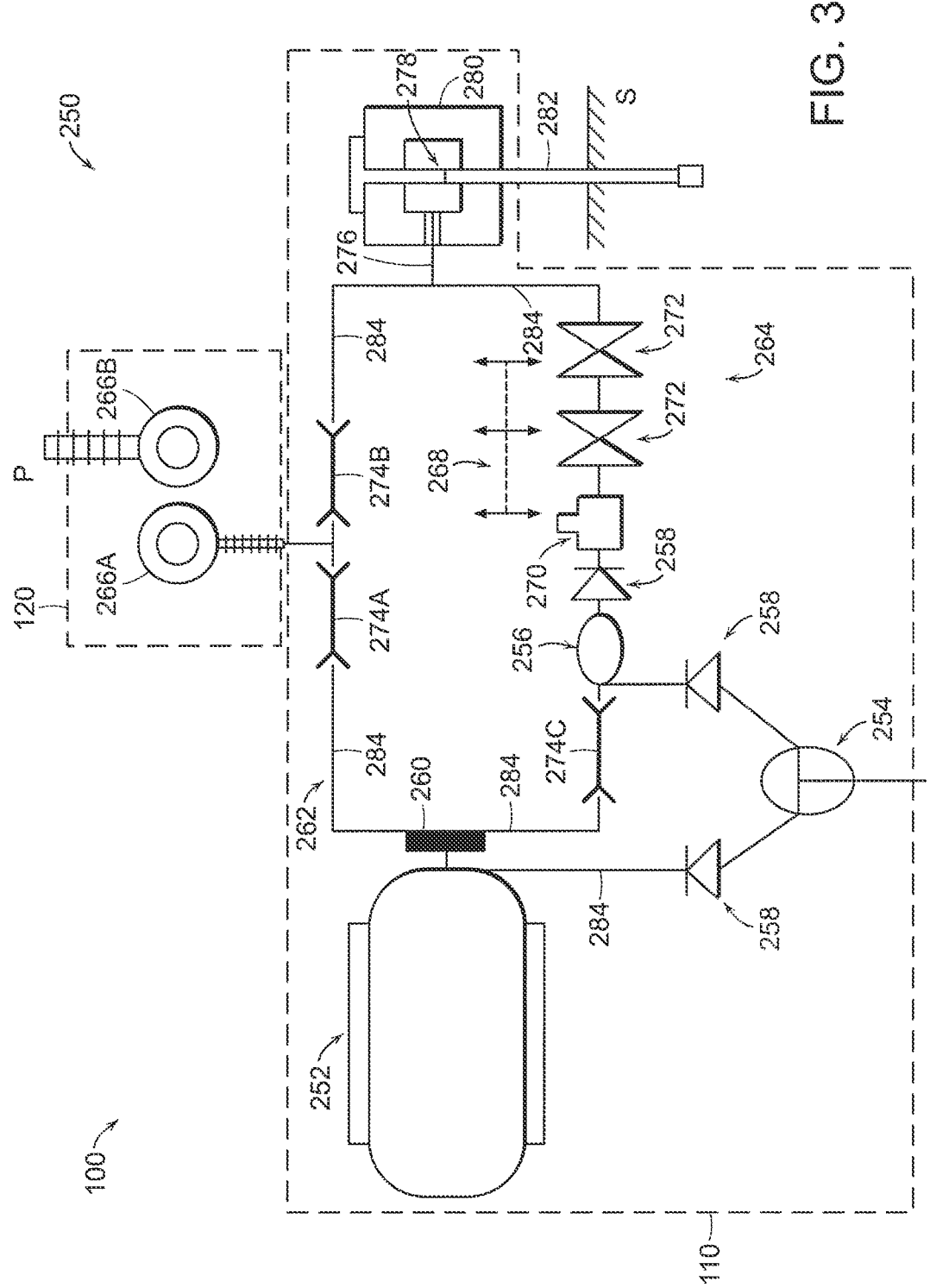
FIG. 3 is a schematic diagram of an exemplary infusion device micro-fluidic circuit in accordance with one embodiment of the invention.

FIG. 3 is a schematic diagram of an exemplary infusion device micro-fluidic circuit 250 that may be incorporated into the fluid medicament delivery device 100 described herein. Other infusion devices having micro-fluidic circuits are described in U.S. Patent Application Publication No. 2005/0165384, published Jul. 28, 2005, the disclosure of which is hereby incorporated by reference herein in its entirety. The micro-fluidic circuit 250 includes a pressurized reservoir 252 that is, in this case, an elastomer bladder. Alternatively, a flexible vessel or bag compressed by a spring may be utilized. A fill port 254 is used to introduce fluid, such as insulin, to the micro-fluidic circuit 250. In this micro-fluidic circuit 250, introducing insulin via the fill port 254 fills both the reservoir 252 and a variable-volume bolus reservoir 256. Check valves 258 prevent backflow of insulin in a number of locations.

During use, insulin is forced from the reservoir 252 by elastic contraction of the elastomer, through a filter 260, and into two parallel flowpaths, a basal flowpath 262 and a bolus flowpath 264. The basal flowpath 262 delivers a constant dose or steady-state level of insulin to a patient; the bolus flowpath 264 delivers a bolus dose of insulin to the patient as needed or desired by the patient, for example, in conjunction with a meal. The basal flowpath 262 includes a first pressure sensor 266A or other pressure or flow sensors in communication with the flowpath 262, for example, at a mid-point in the basal flowpath. In an alternative embodiment, the first pressure sensor 266A or first sensing element 262 may be placed further upstream or downstream in the basal flowpath, as desired. In another alternative embodiment, a plurality of pressure sensors in communication with the basal flowpath 262 may be utilized. A second pressure sensor 266B or second sensing element is exposed to ambient air pressure P. The function of and relationship between the pressure sensors 266A, 266B is described in more detail below. In one embodiment, the pressure sensors 266A, 266B consist of micro-electronic-mechanical system (MEMS) sensors. Each MEMS sensor is about 2 mm square but sensors having different dimensions may also be used. Both MEMS sensors are contained within the indicator unit 120. In FIG. 3, the pressure sensor 266A communicates with a portion of the basal circuit 262 between two flow restrictors 274A, 274B (e.g., microcapillaries). In one embodiment, this portion between the flow restrictors 274A, 274B may be a pressure sensor chamber, as described in more detail below. The pressure sensor 266A senses pressure changes in the basal flowpath 262, which may be indicative of occlusion conditions that increase pressure therein. The pressure sensor 266B senses changes in ambient air pressure external to the fluid medicament delivery 100. The pressure sensors 266A, 266B are absolute pressure sensors, but a single relative pressure sensor may also be utilized. A relative pressure sensor, e.g., a gauge MEMs sensor, may be used to replace both absolute pressure sensors.

To deliver a bolus via the bolus flowpath 264, the patient presses a button 268 That drives a single stroke (delivering a single dose) of a bolus displacement chamber 270 and opens two valves 272. The valves 272 are in series for redundancy safety purposes. An optional flow restrictor 274C regulates, in part, the fluid flow through the bolus flowpath 264. The parallel flowpaths 262, 264 join at a common channel 276 just before an internal chamber or a cannula void 278. The cannula void 278 is formed in a cannula base 280, which allows a point of connection to a cannula 282. The cannula 282 extends below the skin S of a patient, thus delivering the insulin subcutaneously. In one embodiment, the actuation of the bolus button 268 may be sensed by the indicator unit 120 with, for example, a magnetic sensor, a Hall effect sensor, or a switch. In an alternative embodiment of the present invention, at least one pressure sensor may be placed in the bolus flowpath 264, thereby allowing the indicator unit 120 to sense the actuation of the bolus button 268. Conduits 284 having diameters larger than those of the flow restrictors 274A, 274B, 274C connect the various components.

Figure 4:
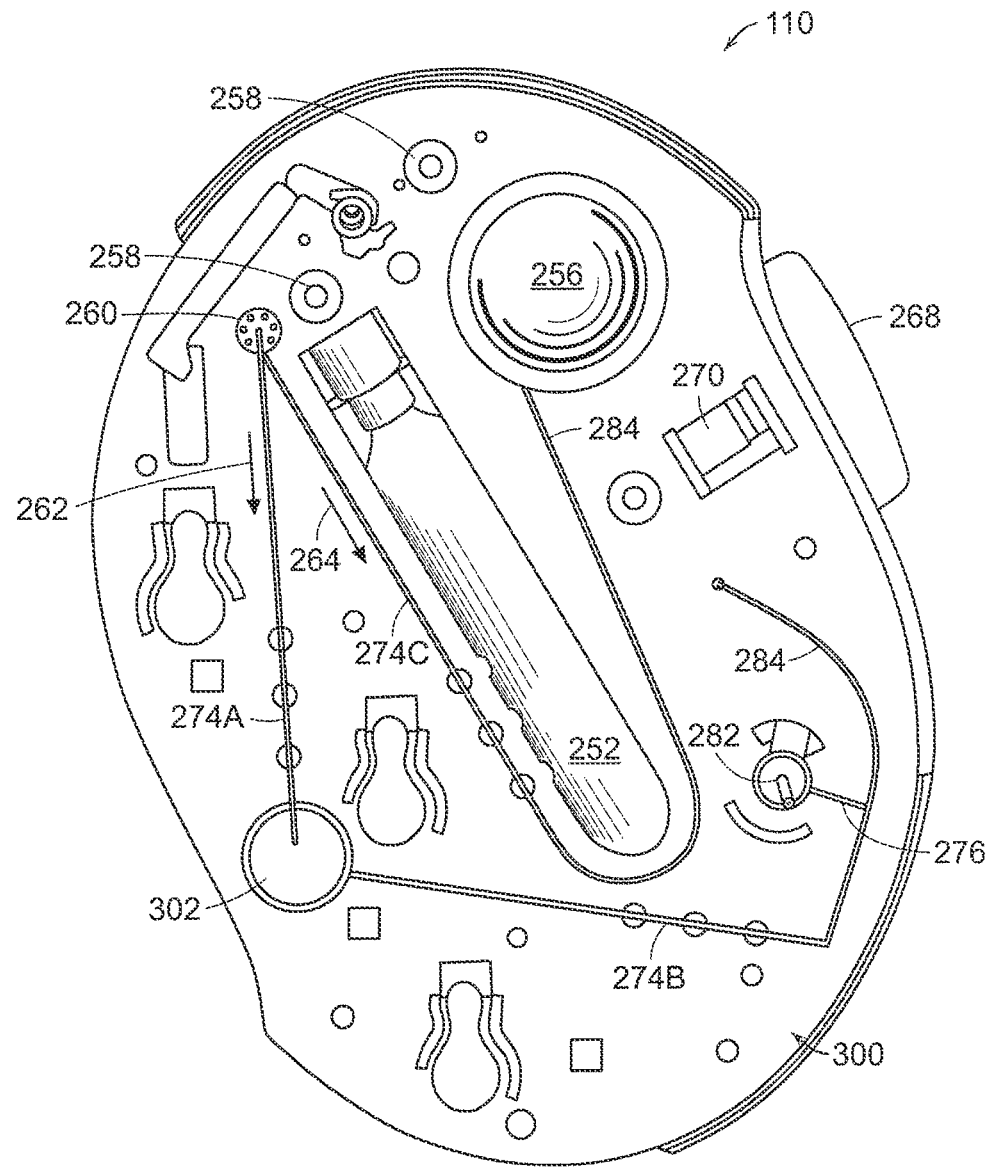
FIG. 4 is a schematic bottom view of a patient attachment unit of the fluid medicament delivery device of FIG. 1 with an external housing removed.

FIG. 4 depicts a bottom view of the patient attachment unit 110 showing the internal components and structures therein, with the housing removed. Specifically, the bottom portion of the housing 110a, to which the attachment interface 116 is secured, has been removed. These internal components and structures correspond generally to the micro-fluidic circuit 250, discussed in FIG. 3. The components and structures in the patient attachment unit 110 may be disposed in or connected to flow manifold 300, which serves as a mounting platform for the various components. Note that not all conduits and flow components are depicted in FIG. 4, as some components may be secured to the opposite side of the manifold 300 or formed therein.

As described above with regard to FIG. 3, insulin in the bolus flowpath 264 (the Bolus flowpath 264, in FIG. 4, is downstream of the labeled arrow) of the micro-fluidic circuit 250 is delivered from the elastomer reservoir 252, filtered through the filter 260, and stored in the variable-volume bolus reservoir 256. In certain embodiment, the elastomer reservoir 252 may have a total volume of about 3200 microliters; the variable-volume bolus reservoir 256 may have a total volume of about 180 microliters to about 260 microliters. Other volumes of the various components are also contemplated. When the fluid pressure in the elastomer reservoir 252 is greater than the fluid pressure in the variable-volume reservoir 256, the variable-volume reservoir 256 will continue to fill, subject to the flow rate dictated at least by flow restrictor 274C in the bolus flowpath 264. Downstream of the variable-volume bolus reservoir 256 is the bolus displacement chamber 270, which may store a single dose of insulin (e.g., about 5, about 10, about 20, or about 25, or greater than about 25 microliters of insulin, in various embodiments). A check valve 258 allows for free flow of insulin from the variable-volume bolus reservoir 256 to the bolus-displacement chamber 270. The check valve 258 prevents backflow during a bolus stroke (i.e., actuation of the bolus button 268).

Actuating the bolus button 268 opens the two valves 272 (See FIG. 3) and empties the entire contents of the bolus displacement chamber 270. Audible, visual, and/or tactile feedback may be provided to the patient to signal that a bolus has been delivered. Releasing the bolus button 268 closes the two downstream valves 272. The displacement chamber 270 is then refilled with insulin from the variable-volume bolus reservoir 256, which is in turn, filled with insulin from the reservoir 252. The bolus flow rate is controlled with a fixed volume-per-stroke of bolus stimulus, i.e., a predetermined volume of insulin-per-stroke. In another embodiment, the bolus flow control rate also may be controlled by a bolus rate flow restrictor. Also, downstream of the filter 260 is the basal flowpath 262 (the basal flowpath 262, in FIG. 4, is downstream of the labeled arrow) of the micro-fluidic circuit 250. The flow restrictors 274A, 274B are located on opposite sides of a pressure sensor chamber 302.

In various embodiments, each flow restrictor 274A, 274B has a length in a range of about 18 mm to about 35 mm. Other lengths of the flow restrictors are also contemplated, for example, from about 10 mm to about 20 mm. The various channels 284 in the manifold 300 may be formed by, for example, laser cutting, and the flow restrictors 274A, 274B may be placed therein. The flow restrictors 274A, 274B may be glued or fused into the channels, though other methods of retention are also contemplated. Exemplary flow restrictors are described in U.S. Patent Application Publication No. 2006/0054230, the disclosure of which is hereby incorporated by reference herein in its entirety. The flow restrictors 274A, 274B are connected to and in fluidic communication with a pressure sensor chamber 302 that includes a flexible member of sensor membrane 302a (See FIG. 7) disposed thereon. The sensor membrane 302a may be generally conterminous with a mating mounting platform 404 (See FIG. 7) of the patient attachment unit 110, as described in more detail below. As the insulin in the basal flowpath 262 flows into the chamber 302, pressure of the insulin within the basal flowpath 262 displaces the sensor membrane 302a. This displacement is sensed by the pressure sensor 266A, as described below. In this manner, the pressure sensor 266A may sense the pressure of the insulin in the basal flowpath via movement of the sensor membrane 302a.

Figure 5:
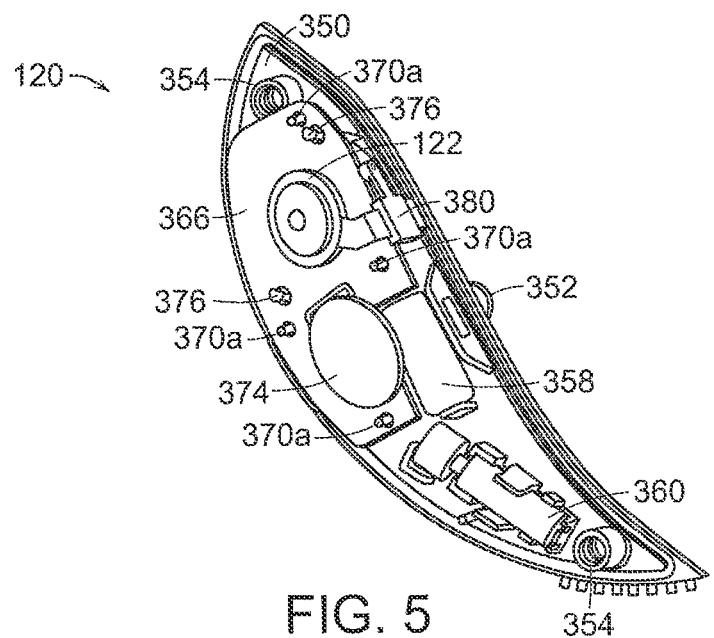
FIG. 5 is a schematic perspective view of an indicator unit of the fluid medicament delivery device of FIG. 1 with an external housing removed.
Figure 6:
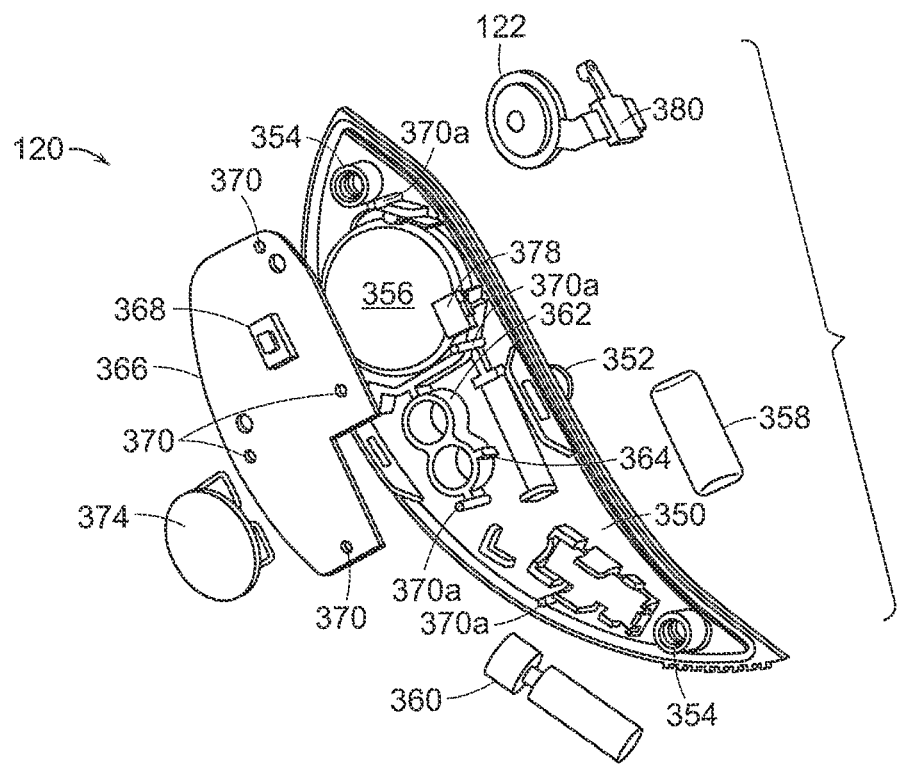
FIG. 6 is a schematic exploded perspective view of the indicator unit of FIG. 5.

FIG. 5 depicts a schematic perspective view of the indicator unit 120 with the top exterior housing 120a removed. FIG. 6 shows an exploded view of the indicator unit 120 depicted in FIG. 5. As discussed herein, the indicator unit 120 may, in certain embodiments, detect changes in pressure within the micro-fluidic circuit 250 contained in the patient attachment unit 110, and perform other test to ensure proper operation of the medicine delivery device 100. The patient may be alerted as necessary via audible, visual, and/or tactile (e.g., vibration) signals. The components to detect pressure changes, process information, and generate signals or alerts to the patient are contained within the indicator unit 120.

The internal components of the separate indicator unit 120 are mounted, either directly or indirectly, to a mounting platform 350, which, in one embodiment, may be the bottom surface of the indicator unit 120. Partially shown extending from the underside of the indicator unit 120 is at least one circular mating projection 352, which is configured to mate with the patient attachment unit 110, as described below. Mounting arms 354 defining hollow interiors are disposed at or near the edges of the mounting platform 350. The mounting arms 354 correspond to and connect to the top exterior housing 120a with screw, snap-fit, press or other types of connections. Also disposed on the mounting platform 350 are a supercapacitor 358, a vibrating motor 360, and two wells 362, 364. Each well 362, 364 defines a hollow geometrical structure, e.g., a cylinder. Overlaid on at least the wells 362, 364 is a printed circuit board (PCB) 366, which may include one or more processors, as well as a test switch 368 disposed thereon. Several apertures 370 formed in the PCB 366 correspond to and align with extensions 370a from the mounting platform 350. The extensions 370a may be melted during manufacturing to secure the PCB 366 thereto. The indicator button 122 aligns vertically over the test switch 364. A piezoelectric sounder 374 or other sound-generating component is located proximate the PCB 366. One or more battery holder solder pins 376 also penetrate the PCB. An activation switch 378 interacts with an activation button 380, which contacts an activation projection 428 (FIG. 7) on the patient attachment unit 110.

Figure 7:
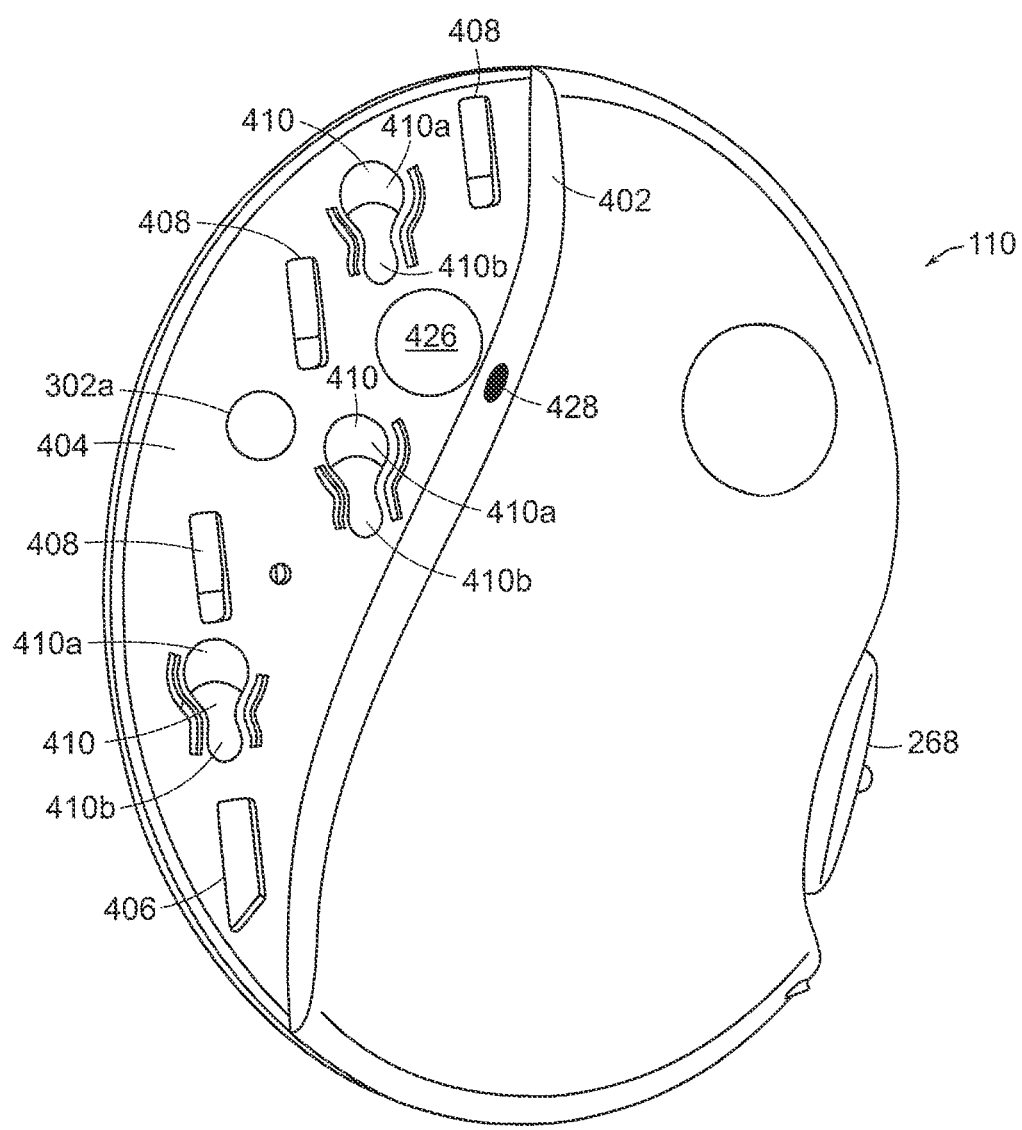
FIG. 7 is a schematic top view of the patient attachment unit of the fluid medicament delivery device of FIG. 1.
Figure 8:
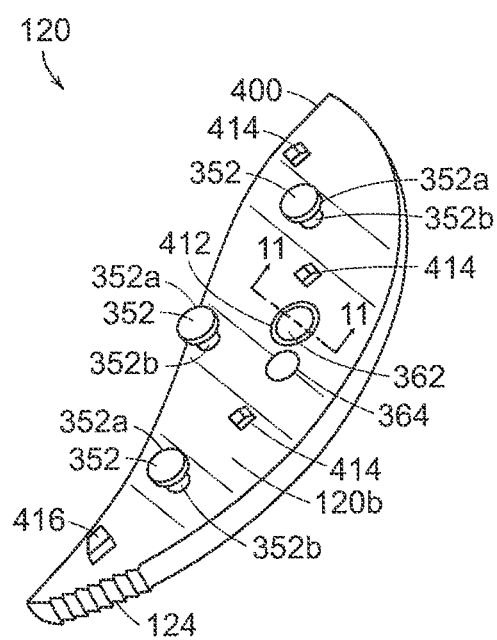
FIG. 8 is a schematic bottom perspective view of the indicator unit of the fluid medicament delivery device of FIG. 1.

FIG. 7 depicts the patient attachment unit 110 and FIG. 8 depicts the underside of the indicator unit 120. The elements that allow for the connection and communication between both units 110, 120 are described below. Indicator unit 120 has a contoured surface 400 that mates with a matching surface 402 of the patient attachment unit 110. The surfaces may be of a undulating curved shape, as shown. Alternative embodiments may utilize crescent, linear, or other shaped surfaces. In another embodiment of the present invention, the contoured surface 400 of the indicator unit 120 may have a vertically-graded slope. The mating shapes of the leading surface 400 and the matching surface 402 assist in properly securing and aligning the indicator unit 120 to the patient attachment unit 110 and help prevent inadvertent detachment of the two units. Further, the complementary shapes of the contoured surface 400 and the matching surface 402 direct the indicator units 120 to move in and out of a locking position, to connect and disconnect the indicator unit 120 from the patient attachment unit 110 while ensuring proper alignment of the operative components.

Proximate the matching surface 402 of the patient attachment unit 110 is a mating mounting platform 404. Multiple apertures 406, 408, and 410 in the mounting platform 404 are configured to receive corresponding mating projections 416, 414, 352 extending from a bottom surface 120b of the indicator unit 120 to secure the two units. The apertures 406, 408, and 410 may have a polygon, oblong, or other shape. Alternative configurations, shapes, and orientations of the apertures 406, 408, 410 and the mating projections 416, 414, 352 are contemplated. The wells 362, 364 are formed in and are substantially coterminous with the bottom surface 120b of the indicator unit 120. In addition, a raised lip 412 circumscribes the well 362 and projects above the bottom surface 120b. The well 362 and the lip 412 are oriented to substantially align with the sensor membrane 302a when the patient attachment unit 110 and indicator unit 120 are connected. The sensor membrane 302a is substantially coterminous with the mating mounting platform 404, and is the top surface of the pressure chamber 302, described above. A pressure equalizing membrane 426 also may be substantially coterminous with the mating mounting platform 404. The function of the pressure equalizing membrane 426 is described below. The activation projection 428 contacts the activation button 380 when the patient attachment unit 110 is connected to the indicator unit 120.

Each of the projections 416, 414, 352 of the indicator unit 120 mate with the corresponding apertures 406, 408, and 410 of the patient attachment unit 110 to form the complete assembled fluid medicament delivery device 100. Specifically, the guiding projection 416 mates with the guiding aperture 406; the aligning projections 414 mate with the aligning apertures 408; and the circular mating projections 352 mate with the asymmetrically oblong apertures 410. Each mating pair has corresponding shapes and corresponding orientations to secure the indicator unit 120 to the patient attachment unit 110. Each of the circular mating projection 352 includes an enlarged end 352a, which is enlarged relative to an extension 352b that projects from the exposed bottom surface 120b of the indicator unit 120. The enlarged end 352a is configured and sized to fit within the enlarged portion 410a of aperture of aperture 410. When completely installed, as described below, the extension 352b is partially surrounded by a constricted portion 410b of the oblong aperture 410.

Figure 9C:
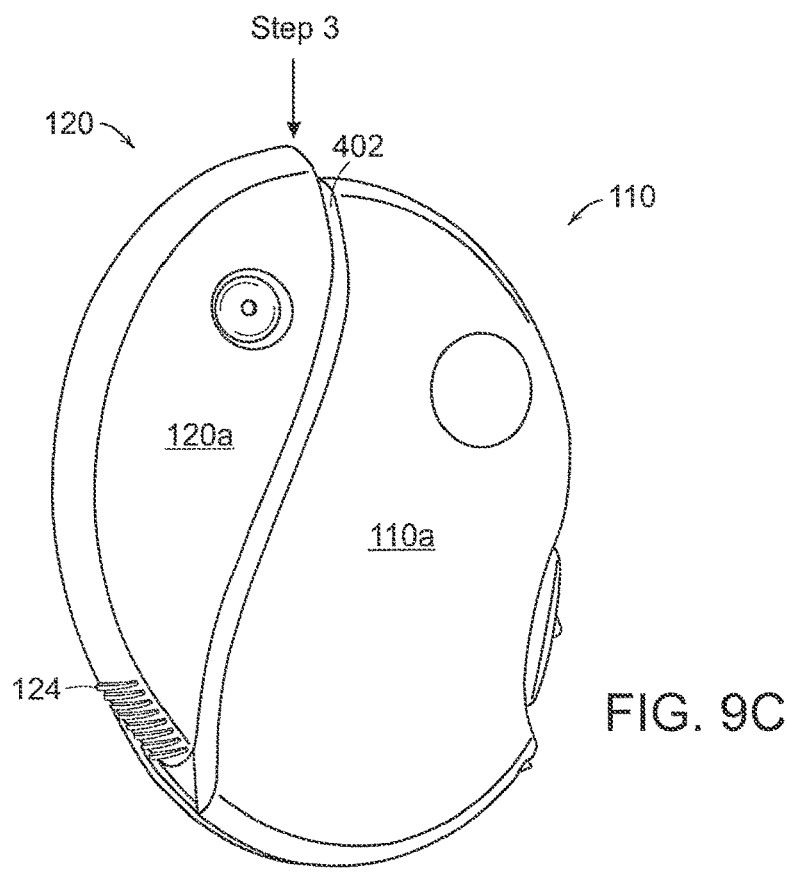
Figure 9D:
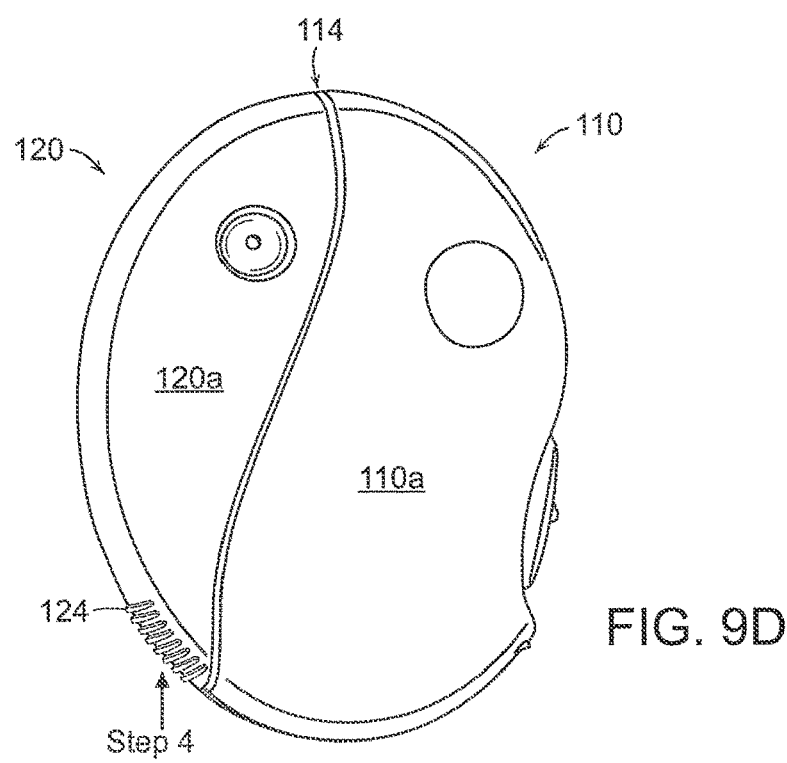

The patient attachment unit 110 and the indicator unit 120 may be secured to and detached from one another as depicted in FIGS. 9A-9D. First, from the initial position depicted in FIG. 9A, the indicator unit 120 is inverted (Step 1) such that the bottom surface 120b is arranged substantially opposite the mounting platform 404, as depicted in FIG. 9B. The indicator unit 120 is then placed (Step 2) in close proximity to the patient attachment unit 110, such that the enlarged ends 352a of the circular mating projections 352 are aligned with and pass through the enlarged portions 410a of the apertures 410. To completely secure the indicator unit 120 to the patient attachment unit 110, the patient slides (Step 3) the indicator unit 120 in an chordal direction, so that the extensions 352b of the mating projections 352 are located within the constricted portion 410b of the apertures 410. The enlarged ends 352a prevent the indicator unit 120 from being inadvertently dislodged from the patient attachment unit 110. To disconnect the indicator unit 120 from the patient attachment unit 110, the patient slides (Step 4) the indicator unit 120 in a direction opposite the direction of Step 3. Textured edge 124 may provide a gripping surface to facilitate this step. The enlarged ends 352a are again aligned with the enlarged portions 410a of the apertures 410, and the two units 110, 120 may be separated.

The indicator unit 120 may be disconnected from the patient attachment unit 110 in response to an occlusion event in the patent attachment unit 110, or due to an electronics failure or low battery charge within the indicator unit 120. Additionally, the two units 110, 120 may be disconnected because insulin in the patient attachment unit 110 may be exhausted or functionally depleted after prolonged use. In general, this may occur after a period of time defined at least in part by the volume of the elastomer reservoir 252 or the amount of insulin introduced to the reservoir 252 during filling. In certain embodiments, the elastomer reservoir, when fully filled with insulin, may contain sufficient insulin to dispense as needed for about 24, about 48, about 72, or greater than about 72 hours. Other times are also contemplated, based on the type of medicament being delivered, elastomer reservoir size, delivery schedule, etc. The separate indicator unit 120 alerts the patient when insufficient levels of insulin remain in the patient attachment unit 110. When the insulin supply in the elastomer reservoir 252 is exhausted or functionally depleted, the indicator unit 120 may be disconnected from the patient attachment unit 110 and the patient attachment unit 110 may be disposed of. Another patient attachment unit 110 may be obtained, filled with insulin and connected to the separate indicator unit 120, which may be re-used as long as it has sufficient battery power. Alternatively, the exhausted or functionally depleted patient attachment unit 110 may be refilled via the fill port 252.

Figure 10:
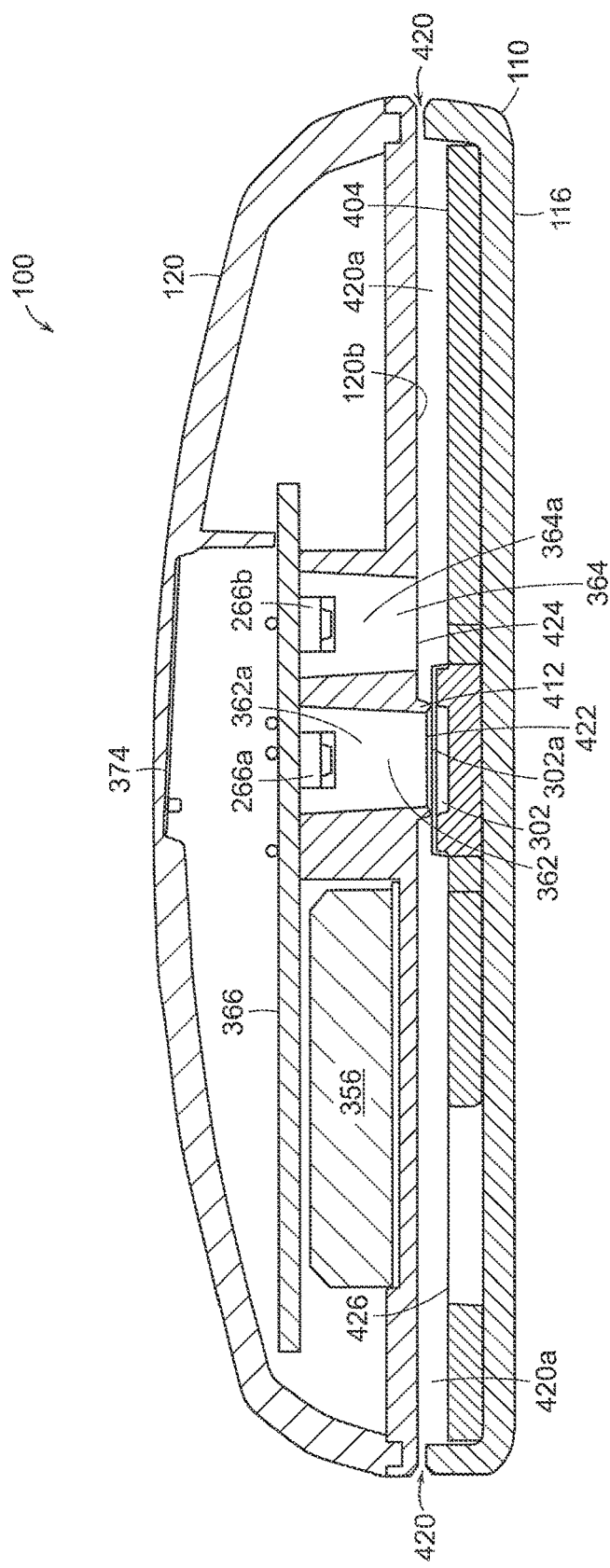
FIG. 10 is a schematic section view of the fluid medicament delivery device of FIG. 1 taken along line 10-10.

Depicted in FIG. 10 is a cross-sectional view of the assembled fluid medicament delivery device 100, depicting a number of internal components, including the piezoelectric sounder 374, and the PCB 366, the battery 356, and the wells 362, 364. For clarify, many of the various conduits and components contained within the patient attachment unit 110 are not depicted. This figure is used to show the general mating relationship between the two units 110, 120. When the indicator unit 120 is secured to the patient attachment unit 110, the bottom surface 120*b* of the indicator unit 120 is in close proximity but slightly spaced from the mounting platform 404, with the exception of the raised lip 412 of the well 362. The raised lip 412 of the well 362 contacts the sensor membrane 302*a* of the patient attachment unit 110. In alternative embodiments, other portions of the bottom surface 120*b* may contact the mounting platform 404. The pressure sensors 266A, 266B are mounted to the PCB 366 and disposed in the wells 362, 364, respectively. Each well is filled with a substance to transmit effectively pressure, for example, a solid resilient gel 362*a*, 364*a* manufactured of silicone gel, for example as manufactured by Dow Corning Corporation as product no. 3-4241. In general, silicone gels having a shore hardness of about 60 Shore 00 will produce satisfactory results. Other gels may also be utilized. During manufacture, to prevent leakage of the gel at the interface of the PCB 366 and wall of the wells 362, 364, a portion of the gel 362*a* is placed in each well 362, 364, and allowed to solidify. The remainder of the wells 362, 364 is then completely filled with the gel 362*a*, which is in turn, allowed to harden. A meniscus 422 of the gel 362*a* in the well 362 extends to the edge of the raised lip 412. Accordingly, when the patient attachment unit 110 and the indicator unit 120 are connected, the meniscus 422 of the gel 362*a* contacts the sensor membrane 302*a*. The contact between the gel 362*a* and sensor membrane 302*a* allows both to move in relation to one another. As fluid pressure increases within the pressure chamber 302, the sensor membrane 302*a* is forced against the meniscus 422. This pressure is transmitted through the gel 362*a* to the sensor 266A. In an alternative manufacturing process, the wells 362 may be inverted and filled from the underside, with the PCB 366 placed on the wells 362 prior to curing of the gel.

Also shown in FIG. 10 is an ambient air channel 420, which is formed when the indicator unit 120 is attached to the patient attachment unit 110. Since the mounting platform 404 and the bottom surface 120*b* are generally not in contact, ambient air pressure may be transmitted freely into an interstitial space 420*a* between the two units 110, 120. This exposes both a surface or meniscus 424 of the gel 364*a* in the well 364 and the pressure equalizing membrane 426 to ambient air pressure P external to the device 100. This allows the device 100 to sense changes in ambient air pressure, as described below.

Figure 11:
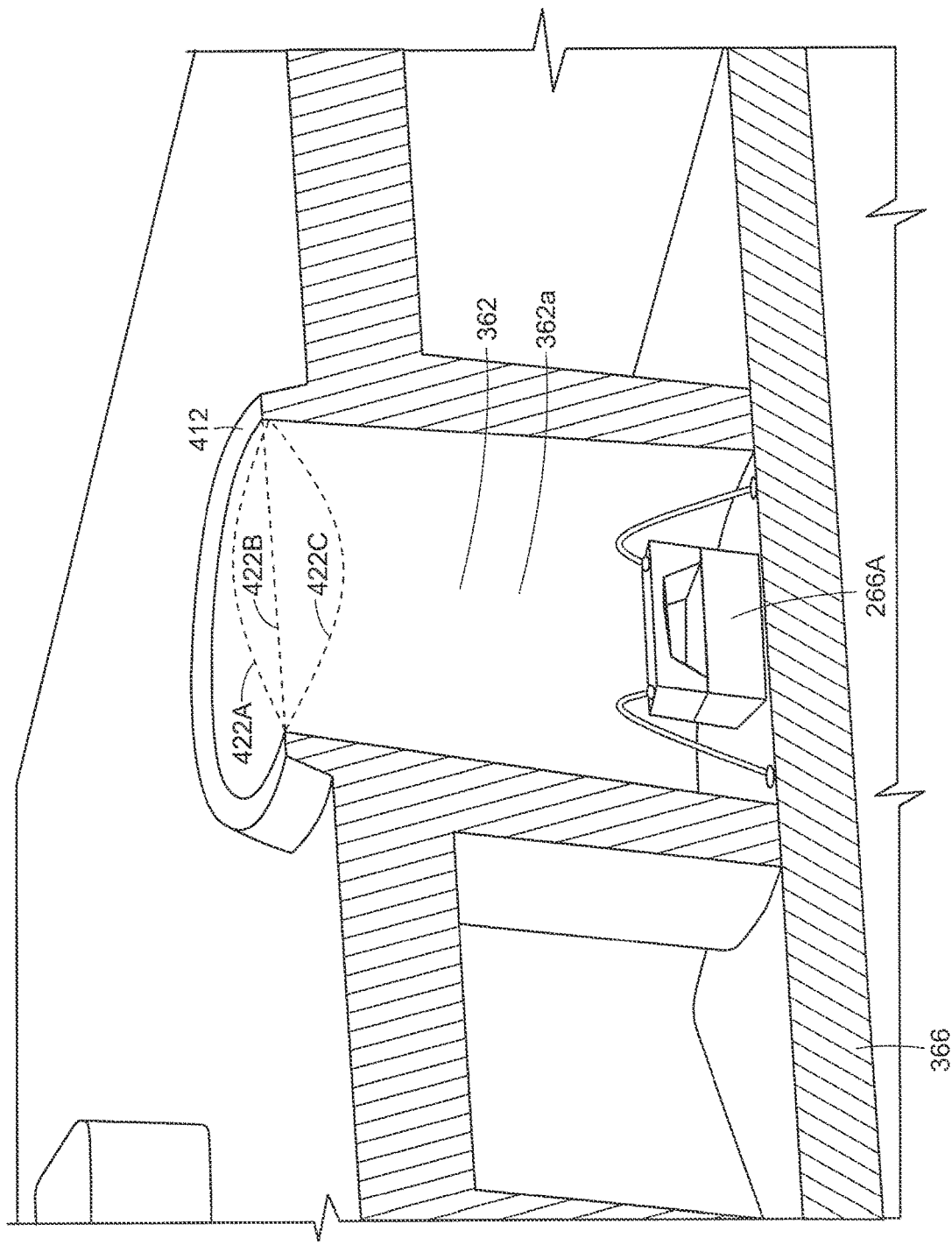
FIG. 11 is a partial schematic section view of a well of FIG. 8 taken along line 11-11.

FIG. 11 depicts an enlarged inverted cross-sectional view of the well 362. The pressure sensor 266A is mounted on the PCB 366 at the base of the well 362. As described above, the gel 362*a* is filled to the edge of the raised lip 412. Three dashed lines 422A, 422B, and 422C illustrate the meniscus 422 of the gel 362*a* according to various conditions. Line 422A illustrates over-filling of the gel 362*a*; line 422B illustrates desired filling of the gel 362*a*; line 422C illustrates under-filling of the gel 362*a*. When the gel 362*a* is filled to the desired level (i.e., coplanar with the raised lip 412) the meniscus 422B is proximate with the sensor membrane 302*a*, while transferring little or no force between the two elements. Force transmission remains minimal or nonexistent until fluid fills the pressure chamber 320. The raised lip 412 minimizes the initial distance between the meniscus 422B and the sensor membrane 302*a*. If the gel 362*a* has been over-filled, the meniscus 422A may exert force on the sensor membrane 302*a*, which may lead to inaccurate sensing. If the gel 362*a* has been under-filled, the sensor membrane 302*a* may not contact the meniscus 422C, again leading to inaccurate sensing.

Figure 12:
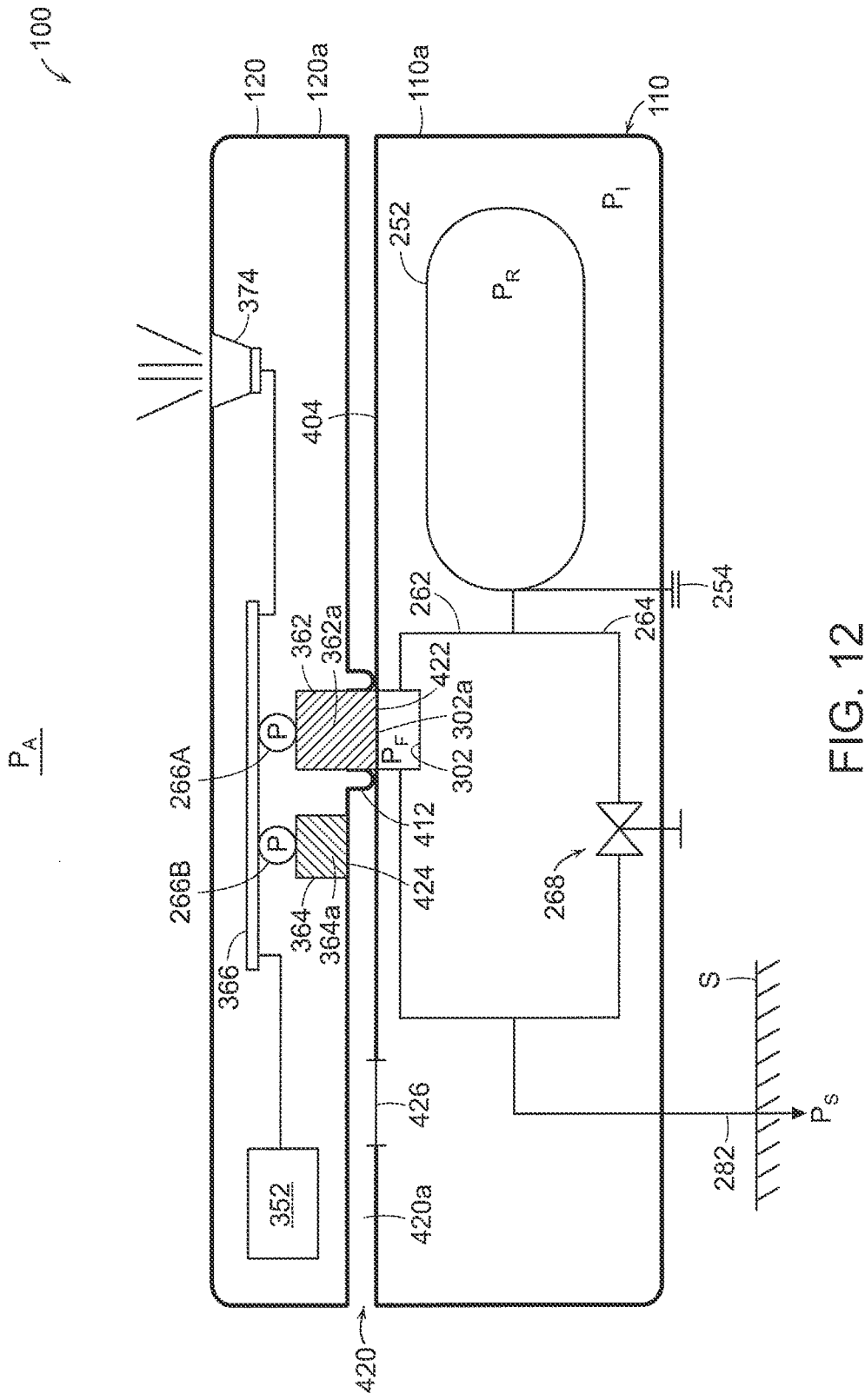
FIG. 12 is a schematic section view of a fluid medicament delivery device in accordance with another embodiment of the present invention.

FIG. 12 depicts a simplified, schematic view of the fluid medicament delivery device 100 to illustrate the interrelationships between, as well as the functionality of, the various components according to one embodiment of the device 100. The patient attachment unit 110 includes a simplified, schematic version of the micro-fluidic circuit depicted in FIG. 3, contained within the housing 110*a*. The flexible pressure equalizing membrane 426 is disposed within and substantially coterminous with the mounting platform 404. The patient attachment unit 110 includes the reservoir 252, for example, an elastomer bladder. The fill port 254 may be used to introduce insulin into the reservoir 252. Insulin displaced from the reservoir 252 fills the basal flowpath 262 and the bolus flowpath 264. Insulin flows through the bolus flowpath 264 and into the patient via the cannula 282 when the bolus button 268 is actuated. Insulin in the basal flowpath 262 flows through the pressure sensor chamber 302, which includes a sensor membrane 302*a*, which is substantially coterminous with the top portion of the mounting platform 404 of the patient attachment unit 110. Insulin from the basal flowpath 262 and bolus flowpath 264 is introduced subcutaneously into the patient via the cannula 282.

The simplified, schematic version of the indicator unit 120 includes the PCB 366, which is powered by the battery 352. The piezoelectric sounder 374 and/or a light, such as a LED, is connected to the PC 366. Also mounted on the PCB 366 are the pressure sensors 266A, 266B, which are each disposed in the wells 362, 364, respectively. The well 364 depicted on the right in FIG. 12 includes the raised lip 412. Each well 362, 364 is filled with the gel 362*a*, 364*a*, such that the meniscus 422, 424 is formed thereon.

When the indicator unit 120 is attached to the patient attachment unit 110, the ambient air channel 420 and the interstitial space 420*a* is formed therebetween. Note that the various connecting elements are not depicted. Both the meniscus 424 of the gel 364*a* and the flexible pressure equalizing membrane 426 of the patient attachment unit 110 are exposed to the ambient pressure $P_A$ in the interstitial space 420*a*.

As insulin in the basal flowpath 262 flows through the pressure sensor chamber 302, when insulin pressure is greater than ambient pressure, the insulin in the filled pressure sensor chamber 302 will flex the sensor membrane 302a outwards. This outward deflection will, in turn, apply pressure to the meniscus 422 of the gel 362a, thus transmitting that pressure to pressure sensor 266A. The PCB 366 interprets the pressure increase and, if required, alerts the patient, e.g., via the piezoelectric sounder 374 and/or the light.

Changes in pressure conditions in the basal flowpath that may occur for at least several reasons: (1) due to an occlusion or partial occlusion downstream of the pressure sensor chamber 302; (2) due to an occlusion or partial occlusion upstream of the pressure sensor chamber 320; or (3) due to a pressure spike inherent in the last phase of contraction of the elastomer reservoir 252. An occlusion or partial occlusion causes the basal flow to stop or partially stop. A pressure spike from the elastomer reservoir 252 occurs when the reservoir 252 is approaching the limit of the reservoir's ability to continue the flow of insulin. During contraction, the elastomer reservoir 252 maintains a substantially constant pressure on the insulin delivered via the basal flowpath 262. However, as the reservoir 252 nears its fully contracted state, the wall applies move force to the insulin, temporarily increasing the pressure until the wall achieves a final rest condition and the insulin pressure equalizes with that of the subcutaneous pressure of the patient. These pressure relationships are described in more detail below.

The indicator unit 120 may be programmed to conduct a pressure reading periodically, for example, about every 30 minutes, to monitor the function of the fluid medicament delivery device 100. This allows for low power consumption and provides for longer life of the battery 352. Periodic pressure readings allow the indicator unit 120 to alert the patient to, and differentiate between, a change in fluid pressure caused by occlusions/partial occlusions and a change in fluid pressure caused by the last contraction phase of the elastomer reservoir 252. As described in more detail below, the electronic components contained within the indicator unit 120 may determine that a change in a pressure during the early operational life of the device 100 is due to an occlusion (e.g., a blocked cannula 282). Further, the indicator unit 120 may determine that a change in pressure during the late stages of operation of the device 100 is due to the last contraction phase of the elastomer reservoir 252. Regardless, upon detection of a pressure change of a predetermined threshold valve, the patient will be alerted that the device 100 is not working properly and that the patient attachment unit 110 needs to be replaced.

The fluid medicament delivery device 100 may operate properly in various external pressure environments, for example, while a patient is at sea-level, at elevated pressure conditions (i.e., below sea-level), and at decreased pressure conditions (i.e., above sea-level). Additionally, due to the functionality described below, the components contained within the indicator unit 120 are able to distinguish pressure changes caused by occlusions from those caused by changes in ambient pressure. The fluid medicament delivery device 100 will continue operating normally in various external pressure environments and, thus, alert the patient to changes in pressure that are only due to conditions that require attention to the device 100 (e.g., an occlusion, a partial occlusion, or a near-empty condition of the elastomer bladder 252).

As described above, the indicator unit 120 includes two pressure sensors 266A, 266B that are both absolute pressure sensors. When the indicator unit 120 and patient attachment unit 110 are connected, the pressure sensor 266B is exposed to ambient air pressure $P_A$, Table 1 depicts known conditions for ambient pressure $P_A$, subcutaneous (below the skin surface S) pressure $P_S$ of a human body, and reservoir pressure $P_R$. These pressures are given at sea-level, 1 meter below sea-level, and 3000 meters above sea-level. As an initial matter, due to the presence of the pressure equalizing membrane 426, the ambient pressure $P_A$ equals the device internal pressure $P_I$. The human body is also pressurized relative to the ambient air pressure $P_A$. such that the subcutaneous pressure $P_S$ of the human body may be calculated as a combination of the ambient pressure and about 10 mbar. The reservoir pressure $P_R$ exerted against the fluid contained therein may be calculated as the combination of the internal device pressure $P_I$ and about 820 mbar (i.e., the pressure exerted directly against the fluid by the elastomer bladder material). The pressure exerted by the elastomer bladder material may be greater than or less than 820 mbar, depending on the material used.

TABLE 1

Known Pressures for Use in Device Operation

| All pressures in mbar | Ambient Pressure $P_A = P_I$ | Subcutaneous Pressure $P_S = P_A + 10$ | Reservoir Pressure $P_R = P_I + 820$ |
| --- | --- | --- | --- |
| Pressure at Sea-Level | 1013 | 1023 | 1833 |
| Pressure at 1.0 meter submersion | 1113 | 1123 | 1933 |
| Pressure at 3000 meters altitude | 800 | 810 | 1620 |

Further, the fluid pressure $P_F$ is sensed at pressure sensor 266A because the meniscus 422 of the gel 362a contacts the sensor membrane 302a of the pressure sensor chamber 302 through which the insulin flows. Table 2 depicts fluid pressures $P_F$ at sea-level, 1 meter below sea-level, and 3000 meters above sea-level. Under Normal (i.e., unblocked) conditions, the fluid pressure $P_F$ at the pressure sensor 266A is the average of the subcutaneous pressure $P_S$ and the reservoir pressure $P_R$. Table 2 also depicts fluid pressure $P_F$ at complete occlusion and partial occlusion (so-called "half-blocking") conditions both upstream and downstream of the pressure sensor chamber 302. Half-blocking conditions may occur when a flow channel or a flow restrictor has a partial occlusion, allowing passage of inclusion at only one-half of its rated flow rate.

TABLE 2

Fluid Pressures at Operational Conditions

| All pressures in mbar | Normal $P_F = (P_S + P_R)/2$ | Upstream Occlusion $P_F = P_S$ | Upstream Half-blocking $P_F = (2 * P_S + P_R)/3$ | Downstream Occlusion $P_F = P_R$ | Downstream Half-blocking $P_F = (P_S + 2 * P_R)/3$ |
|---|---|---|---|---|---|
| Pressure at Sea-Level | 1428 | 1023 | 1293 | 1833 | 1563 |
| Pressure at 1.0 meter submersion | 1528 | 1123 | 1393 | 1933 | 1663 |
| Pressure at 3000 meters altitude | 1215 | 810 | 1080 | 1620 | 1350 |

Table 3 depicts pressure differentials ΔP at sea-level, 1 meter below sea-level, and 3000 meters above sea-level. Generally, a Normal pressure differential ΔP may be about 450 mbar ±about 15%. In one embodiment, a pressure differential ΔP between fluid pressure $P_F$ and ambient pressure $P_A$ from about 344 mbar to about 517 mbar at, below, or above sea-level, is considered normal. A pressure differential ΔP below about 344 mbar is considered a first failure state, generally caused by an upstream (of the pressure sensor chamber 302) occlusion, partial occlusion, or near-empty elastomer bladder condition. A pressure-differential ΔP above about 517 mbar is considered a second failure state, generally caused by a downstream (of the pressure sensor chamber 302) occlusion or partial occlusion. The uniform pressure differentials for each failure condition (i.e., upstream and downstream occlusion, upstream and downstream half-blocking) allow the device to differentiate between the various failure conditions. Information regarding the various failure conditions may be stored in the components within the indicator unit 120, for later download to a computer for device-diagnostic or other purposes.

TABLE 3

Pressure Differentials at Operational Conditions

| All pressures in mbar | Normal $\Delta P = P_F\text{-}P_A$ | Upstream Occlusion $\Delta P = P_F\text{-}P_A$ | Upstream Half-blocking $\Delta P = P_F\text{-}P_A$ | Downstream Occlusion $\Delta P = P_F\text{-}P_A$ | Downstream Half-blocking $\Delta P = P_F\text{-}P_A$ |
|---|---|---|---|---|---|
| Pressure at Sea-Level | 415 | 10 | 280 | 820 | 550 |
| Pressure at 1.0 meter submersion | 415 | 10 | 280 | 820 | 550 |
| Pressure at 3000 meters altitude | 415 | 10 | 280 | 820 | 550 |

The pressure-equalizing membrane 426 allows the device to accurately sense pressures and analyze the various pressure conditions during operation, either at, above, or below sea-level. Consider a proposed insulin infusion device that lacks a pressure equalizing membrane (depicted as 426 in FIG. 12). Table 4 depicts known conditions for ambient pressure $P_A$, internal device pressure $P_I$, subcutaneous pressure $P_S$ of a human, and reservoir pressure $P_R$. These pressures are given at sea-level, 1 meter below sea-level, and 3000 meters above sea-level. Since a pressure equalizing membrane is not utilized, the internal device pressure $P_I$ remains constant (in this case, at the environmental pressure at which the device was manufactured, e.g., sea-level). In certain devices, the internal pressure $P_I$ may be elevated, if the device was manufactured in a clean room, for example, which typically has a pressure higher than the ambient pressure of the location where the clean room is contained. Regardless, the constant internal pressure $P_I$ has a direct effect on the reservoir pressure $P_R$, as shown in Table 4.

TABLE 4

Known Pressures for Use in Device Operation (No Pressure-Equalizing Membrane)

| All pressures in mbar | Ambient Pressure $P_A$ | Internal Pressure $P_I$ | Subcutaneous Pressure $P_S = P_A + 10$ | Reservoir Pressure $P_R = P_I + 820$ |
|---|---|---|---|---|
| Pressure at Sea-Level | 1013 | 1013 | 1023 | 1833 |
| Pressure at 1.0 meter submersion | 1113 | 1013 | 1123 | 1833 |
| Pressure at 3000 meters altitude | 800 | 1013 | 810 | 1820 |

Table 5 depicts fluid pressures $P_F$ at sea-level, 1 meter below sea-level, and 3000 meters above sea-level, for a device lacking a pressure-equalizing membrane. Fluid pressure $P_F$ at complete occlusion and partial occlusion conditions upstream and downstream of the pressure sensor chamber 302 are also depicted in Table 5.

TABLE 5

Fluid Pressures at Operational Conditions (No Pressure-Equalizing Membrane)

| All pressures in mbar | Normal $P_F = (P_S + P_R)/2$ | Upstream Occlusion $P_F = P_S$ | Upstream Half-blocking $P_F = (2 * P_S + P_R)/3$ | Downstream Occlusion $P_F = P_R$ | Downstream Half-blocking $P_F = (P_S + 2 * P_R)/3$ |
|---|---|---|---|---|---|
| Pressure at Sea-Level | 1428 | 1023 | 1293 | 1833 | 1563 |
| Pressure at 1.0 meter submersion | 1478 | 1123 | 1360 | 1833 | 2395 |
| Pressure at 3000 meters altitude | 1322 | 810 | 1151 | 1833 | 1492 |

Table 6 depicts pressure differentials ΔP at sea-level, 1 meter below sea-level, and 3000 meters above sea-level. As described above, a Normal pressure differential ΔP may be defined as about 450 mbar±about 15%. That is, a pressure differential ΔP from about 344 mbar to about 517 mbar at, below, or above sea-level is considered normal. A pressure differential ΔP below about 344 mbar is considered a first failure state; and pressure differential ΔP above about 517 mbar is considered a second failure state. The pressure differentials depicted in Table 6 show the advantages provided by a infusion device that includes a pressure-equalizing membrane, such as that used with the device described herein. Absence of the pressure equalizing membrane may cause at least three types of problems. First, pressure differentials under Normal (i.e., unblocked) conditions may register as a failure condition (where a failure condition is defined as a pressure differential in excess of 517 mbar). See, for example, the Normal condition pressure at 3000 meters altitude, which is an operational altitude for an airplane. In such a case, the device is operating normally, but the device interprets the pressure differential as a failure condition. The device would signal the patient that the device is not operating properly, which may cause the patient to remove and replace a device that is otherwise operating properly.

Second, a condition that should be interpreted as a failure condition may be overlooked. See, for example, the Upstream Half-blocking condition pressure at 3000 meters altitude. There, the pressure differential fall within the normal range of about 344 mbar to 517 mbar. Thus, the device would not alert the patient to a failure conditions, even though there is blockage within the fluid circuit. This may cause a serious medical condition. Third, as can be seen, the pressure differential are not consistent across the same failure conditions, which would prevent the particular failure condition from being subsequently identified during diagnostics.

Figure 13A:
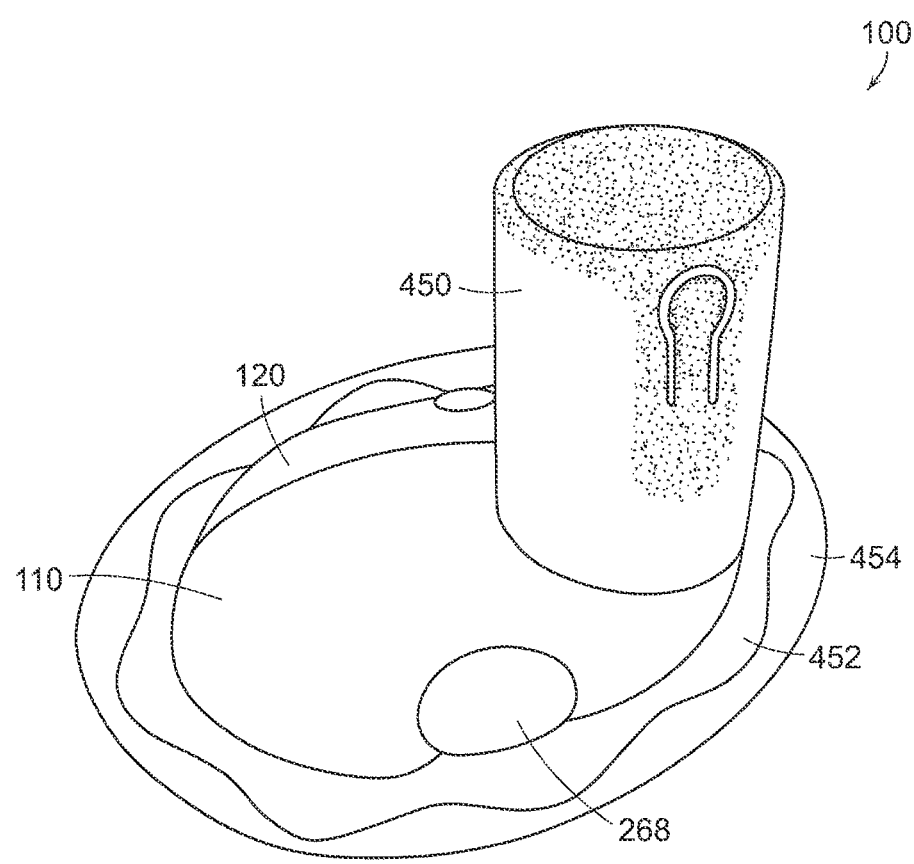
FIGS. 13A-13C depict a procedure for utilizing a fluid medicament delivery device in accordance with one embodiment of the present invention.
Figure 13B:
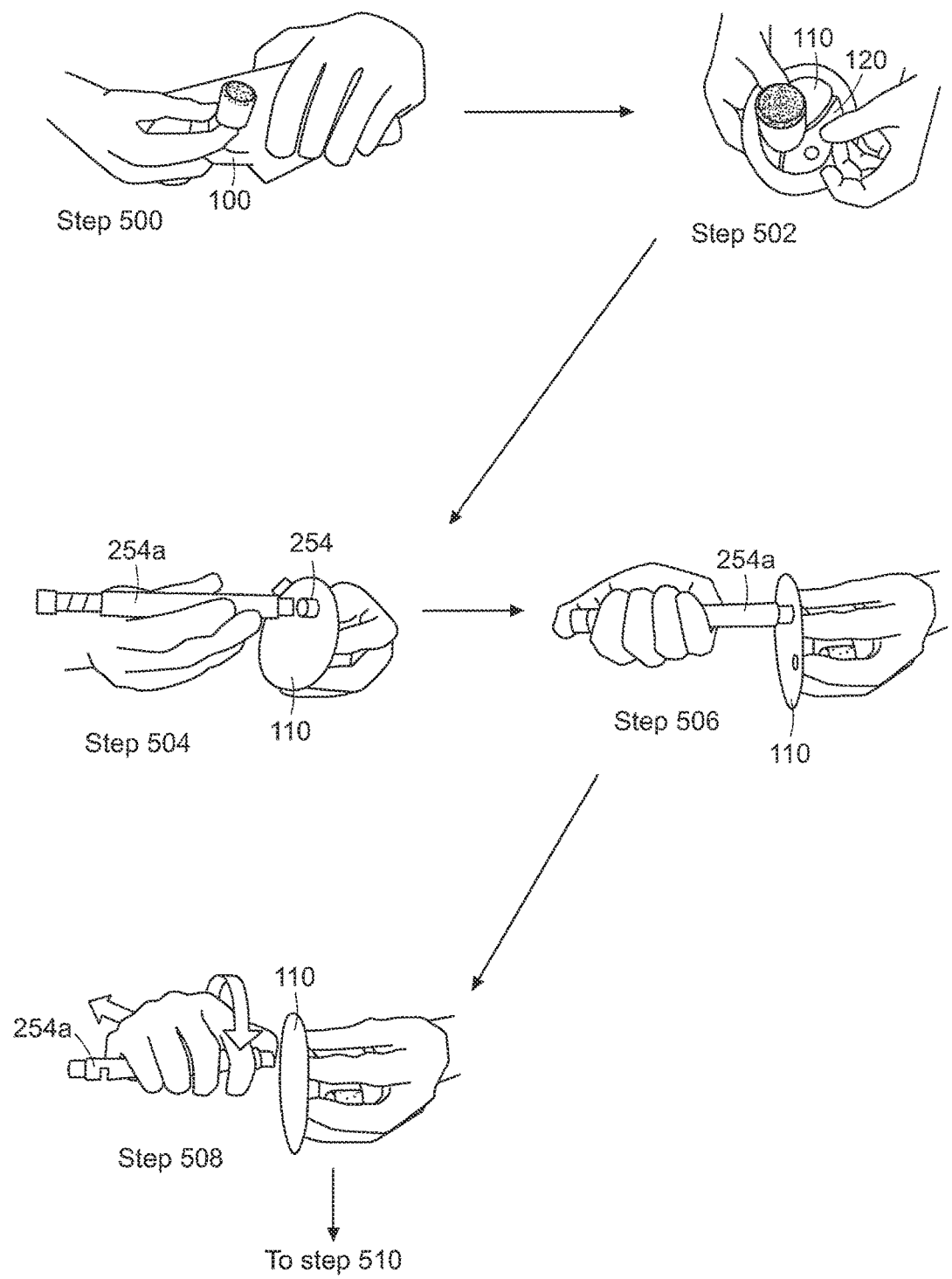
Figure 13C:
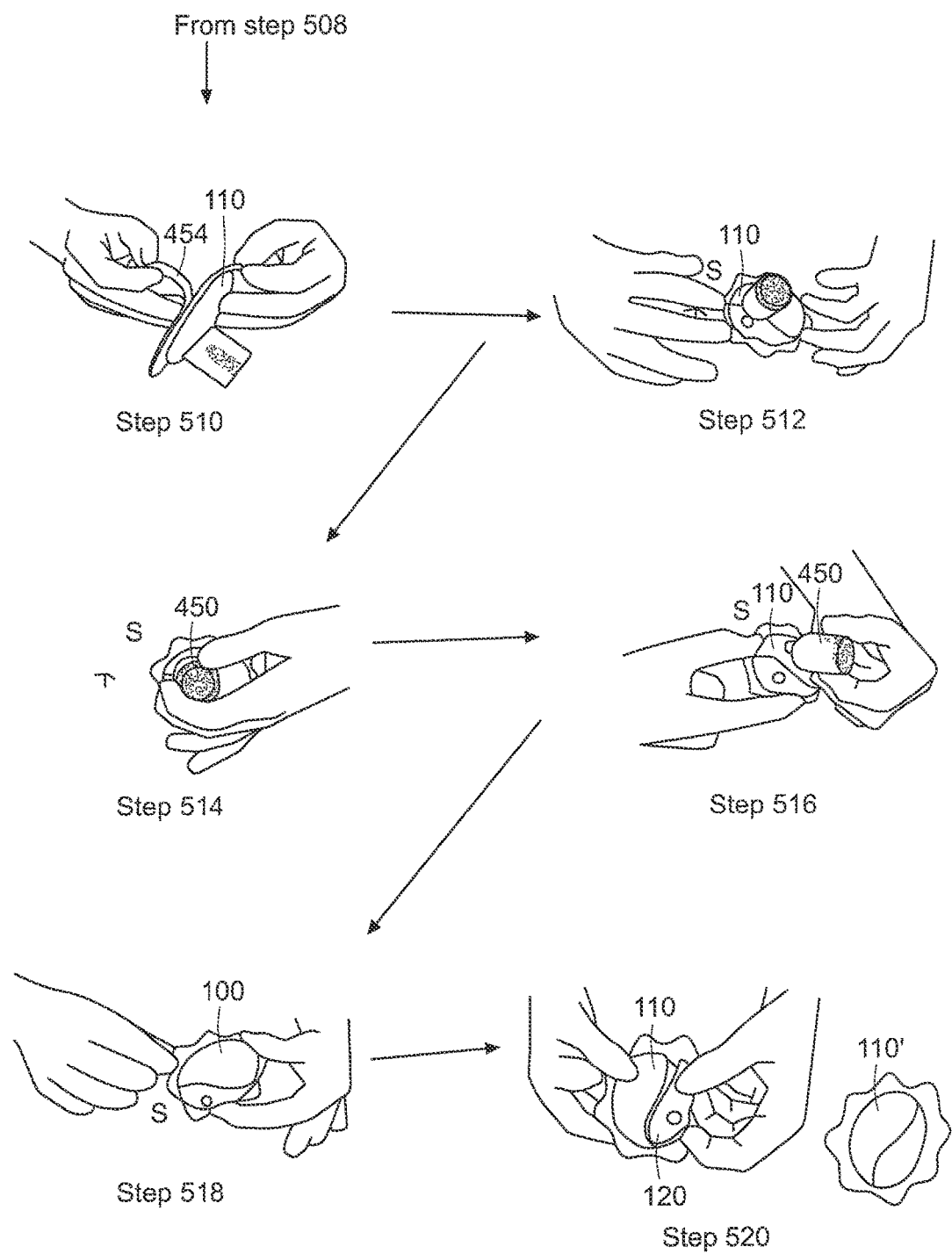

FIG. 13A depicts a perspective view of a fluid medicament delivery device 100 in accordance with an embodiment of the invention. FIGS. 13B-13C depict a procedure for using the fluid medicament delivery device 100. The fluid medicament delivery device 100 includes the patient attachment unit 110 and the separate indicator unit 120. A housing for the cannula insertion device 450 and the bolus button 268 are disposed on the patient attachment unit 110. An adhesive tape 452 for adhering the device 100 to the skin of a patient is disposed on the underside of the patient attachment unit 110. A liner 454 is included to cover the adhesive tape 452 before the device 100 is attached to the patient.

The device 100 is first removed its packaging (Step 500) which keeps the device 100 clean during storage and transport, prior to use. The separate indicator unit 120 is mounted to the patient attachment unit 100 (Step 502), for example, in the manner described above and shown in FIGS. 9A-9C. To fill the device 100 with the insulin (Step 504), an insulin pen 254a is connected to a fill port 254 on the underside of the patient attachment unit 110. Insulin is then dispensed from the pen 254a to fill the insulin reservoir (Step 506). Once full, the insulin pen 254a is disconnected from the device 100 and discarded (Step 508). The liner 454 is then removed from the device 100 to expose the adhesive tape (Step 510). The patient attachment unit 100 is then adhered to an appropriate portion of the patient's skin S (Step 512). Acceptable locations include, but are not limited to, the abdominal area, the area above the buttocks, or the area proximate the triceps muscle. The patient then actuates the cannula insertion device 450 to insert the cannula into the body (Step 514). The patient disconnects the housing of the cannula insertion device 450 from the patient attachment unit 110 (Step 516). The device 100 is now operational and may be worn by the patient during normal, everyday activities. When the device 100 needs to be removed (either due to a failure state or depletion of insulin), the patient peels the

TABLE 6

Pressure Differentials at Operational Conditions (No Pressure-Equalizing Membrane)

| All pressures in mbar | Normal $\Delta P = P_F - P_A$ | Upstream Occlusion $\Delta P = P_F - P_A$ | Upstream Half-blocking $\Delta P = P_F - P_A$ | Downstream Occlusion $\Delta P = P_F - P_A$ | Downstream Half-blocking $\Delta P = P_F - P_A$ |
|---|---|---|---|---|---|
| Pressure at Sea-Level | 415 | 10 | 280 | 820 | 550 |
| Pressure at 1.0 meter submersion | 365 | 10 | 247 | 720 | 1282 |
| Pressure at 3000 meters altitude | 522* | 10 | 351* | 1033 | 692 | device 100 from the skin S (Step 518). As shown in Step 520, the patient may then detach the indicator unit 120 from the patient attachment unit 110, as described above with regard to FIG. 9D. The indicator unit 120 may then be attached to a new patient attachment unit 110. In this way, the comparatively more-expensive indicator unit 120 may be reused, while the less-expensive patient attachment unit 110 may be disposed of.

The various components utilized in the device described herein may be metal, glass, and/or any type of polymer suitable for sterilization and useful for delivering insulin or other medicaments subcutaneously. Polyurethane, polypropylene, PVC, PVDC, EVA, and others, are contemplated for use, as are stainless steel and other medical-grade metals. More specifically, medical-grade plastics may be utilized for the cannula itself, as well as other components that contact or otherwise penetrate the body of the patient. Needless and springs made from medical-grade stainless steel are also desirable, to prevent failure associated with use.

Figure 14:
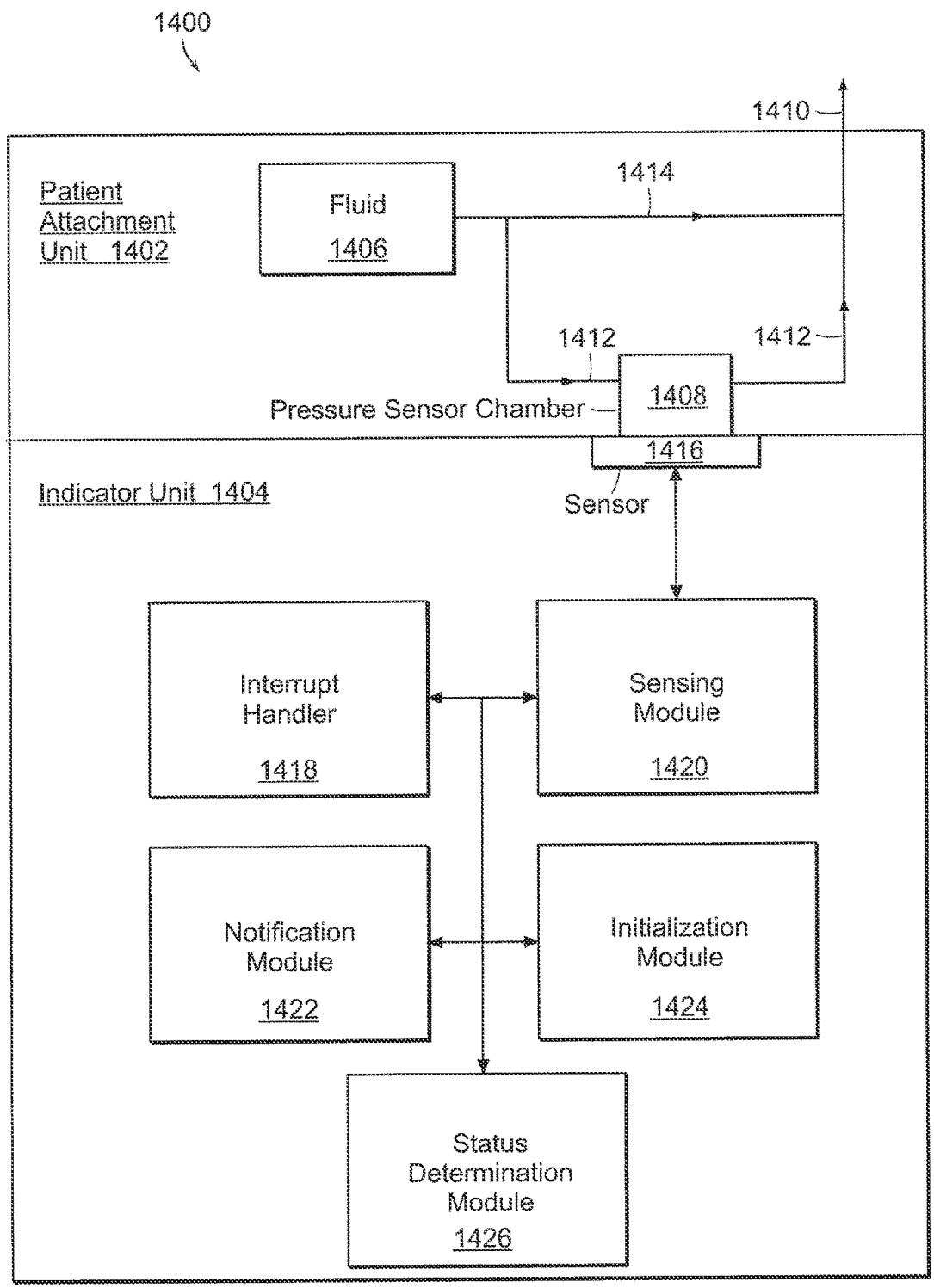
FIG. 14 is a system-level diagram of a fluid medicament delivery device.

FIG. 14 is a block diagram illustrating one embodiment of a fluid medicament delivery device 1400. The device 1400 may include some or all of the features and components of the embodiments of the devices described above, such as the fluid medicament delivery device 100, even if they are not explicitly shown in FIG. 14. Aspects of the fluid medicament delivery device 1400 may be hereinafter described as conceptual blocks or modules, that may encompass some or all of the components described herein. It will be understood by a person of ordinary skill in the art that the illustrated modules may be conceptual, rather than explicit, requirements. For example, two or more modules may be combined into a single module, such that the functions performed by the two or more modules are, in fact, performed by the single module. In addition, it will be understood that any single one of the modules may be implemented as multiple modules, such that the functions performed by any single one of the modules are, in fact, performed by the multiple modules. Moereover, the fluid medicament delivery device 1400 may be modified in a variety of manners without departing from the spirit and scope of embodiments of the invention. As such, the depiction of the fluid medicament delivery device 1400 in FIG. 14 and in other figures is non-limiting.

The fluid medicament delivery device 1400 includes a patient attachment unit 1402 and an indictor unit 1404. The patient attachment unit 1402 includes a fluid reservoir 1406 and a pressure sensor chamber 1408. The fluid reservoir 1406 may include one or more reservoirs. Fluid from the fluid reservoir 1406 passes through the device 1400 via a first path 1412 (e.g., a basal flow path) through the pressure-sensor chamber 1408 and a second path 1414 (e.g., a bolus flow path). A cannula 1410 allows for delivery of the fluid to a patient.

The indicator unit 1404 includes, in one embodiment, a sensor 1416, an interrupt handler 1418, a sensing module 1420, a notification module 1422, an initialization module 1424, and a status determination module 1426. The sensor 1416 may be, for example, the first pressure sensor 266A and/or the second pressure sensor 266B described above, and may sense a pressure of the fluid in the pressure sensor chamber 1408 and/or an ambient air pressure.

Figure 15:
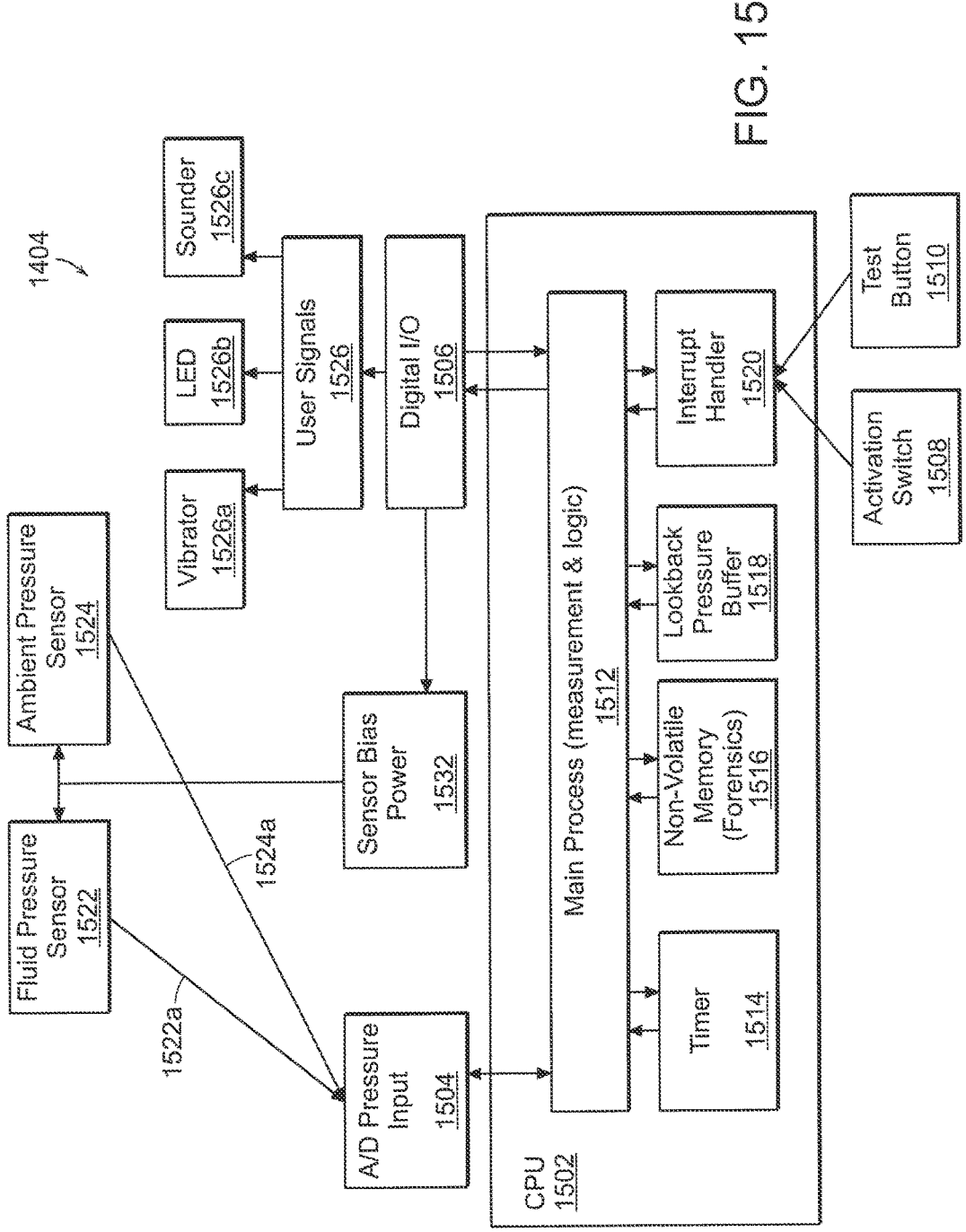
FIG. 15 is a system-level diagram of an indicator unit.

FIG. 15 depicts one embodiment of the indicator unit 1404. A central processing unit (CPU) 1502 is programmed to perform the operations described above, such as conducting a pressure measurement, and other operations described further below. The CPU 1502 may include a processor, memory, storage device, and/or other components typically used in a low-power, embedded CPU, as understood by one of ordinary skill in the art. The CPU 1502 communicates with an analog-to-digital (A/D) pressure input 1504, an digital input/output ("I/O") interface 1506, and actuation devices such as an activation switch 1508 and a test button 1510.

The CPU 1502 may include a main process 1512 that performs measurement and logic analysis and coordinates information with other CPU modules. A timer 1514 my track the passage of time and enable CPU operations to occur at certain times or time intervals. In one embodiment, the timer 1514 is a sample timer and triggers a sample interrupt for initiating a sensor measurement. The sample timer may be configured to expire about every 30 minutes, trigger an interrupt, and reset and count again from zero. In another embodiment, the timer 1514 includes a cycle counter that tracks the number of times the sample timer has expired. The timer 1514 may be capable of counting larger durations of time, for example, up to the 72-hour time limit of use of a patient attachment unit described herein. Other longer and shorter sample time limits are contemplated.

The CPU 1502 may include a non-volatile memory 1516 for storing data. The contents of the non-volatile memory may be preserved, even if the indicator unit is turned off and/or loses battery power. In one embodiment, the CPU 1502 stores forensic data in the non-volatile memory 1516. Similarly, the CPU 1502 may store the results of prior pressure measurements in a lookback pressure buffer 1518, which may include volatile or non-volatile memory. The lookback pressure buffer 1518 may be sized to store the history of every pressure measurement taken for a patient attachment unit life cycle, or may be limited in size and delete older pressure data to accommodate new data.

The CPU 1502 may also include an interrupt handler 1520 for capturing external events, such as the actuation of the activation switch 1508 and the test button 1510, and for generating an interrupt in response. The interrupt handler 1520 may also detect the expiration of the timer 1514 and generate an appropriate interrupt.

The CPU 1502 may also communicate with other input devices, such as a fluid pressure sensor 1522, an ambient pressure sensor 1524, a bolus button sensor, and/or other output devices, such as patient signals 1526 (including a vibrator 1526a, LEDs 1526b, and/or a sounder 1526c). Signals 1522a, 1524a generated by the sensors 1522, 1524 may be analog signals and are, therefore, converted to digital signals with the A/D converter 1504 before the CPU 1502 receives them. Due to the high power requirements of the sensors 1522, 1524, the device 1404 may utilize a sensor bias power unit 1532, which may bias the sensors 1522, 1524 at an appropriate voltage only when a measurement is to be taken, thereby reducing the overall power consumption of the indicator unit 1404. Alternatively, the sensor bias power unit 1532 may be eliminated and the sensors 1522 and 1524 may be powered on a continuous basis. In certain embodiments of the device where battery size is a consideration, this configuration may be less desirable. The CPU 1502 may drive the patient signals 1526 directly or indirectly, using the digital I/O interface 1506. A battery may provide power to the CPU 1502 and other modules.

Figure 16:
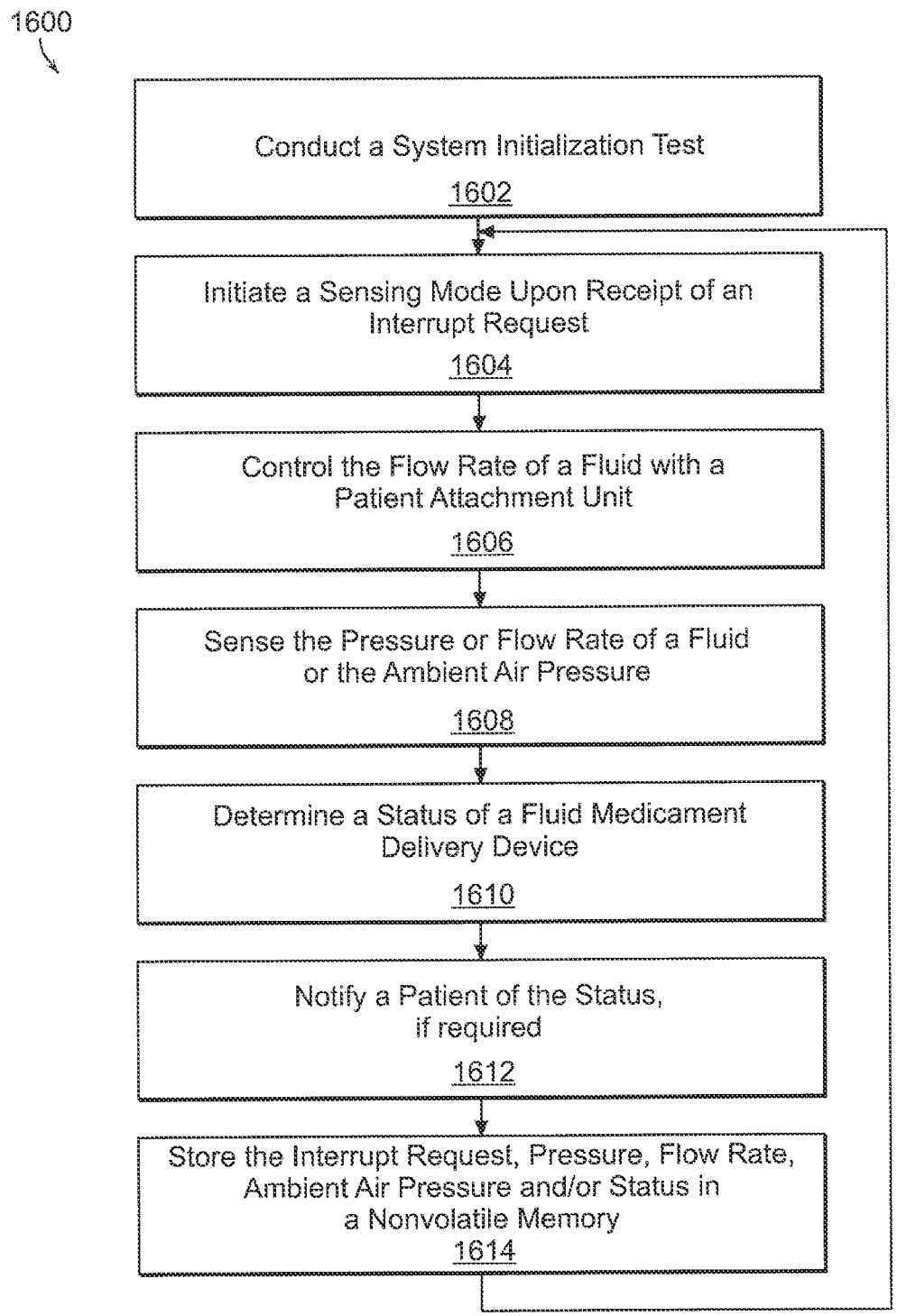
FIG. 16 is a flowchart depicting a method for monitoring a fluid medicament delivery device.

FIG. 16 depicts a method 1600 for monitoring a fluid medicament delivery device. In brief, the method 1600 begins by conducting a system initialization test (Step 1602). Next, a sensing mode is initiated upon receipt of an interrupt request (Step 1604). The flow rate of a fluid is controlled with a patient attachment unit (Step 1606). A parameter of interest of a fluid, such as a flow rate or a fluid pressure, and/or the ambient air pressure is measured (Step

1608). The status of a fluid medicament delivery device is determined (Step 1610), and a patient is notified of the status (Step 1612), if required. Finally, the interrupt request, fluid-pressure, flow rate, ambient air pressure, and/or status may be stored in a non-volatile memory (Step 1614).

Figure 17:
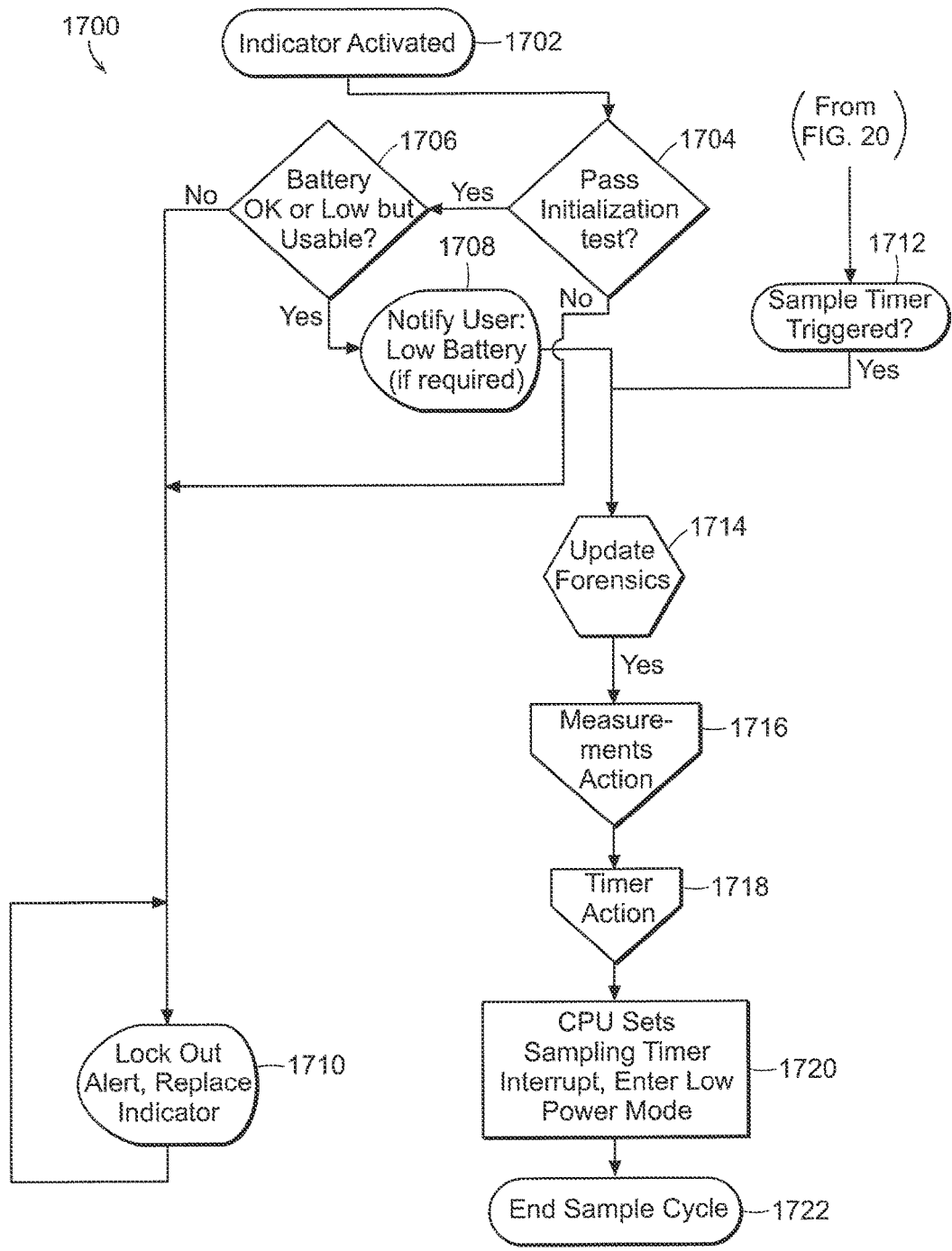
FIG. 17 is a flowchart depicting another embodiment of a method for monitoring a fluid medicament delivery device.

FIG. 17 shows another embodiment of a method 1700 for monitoring a fluid flow with an indicator unit. The method begins by activating the indicator unit (Step 1702). The activation may occur, for example, when the indicator unit is coupled to the patient attachment unit, as a result of a patient-activated button or switch, and/or during product testing. An initialization test is performed (Step 1704), in which the indicator unit may perform hardware integrity diagnostics on its circuitry and electronic components (e.g., perform a test on wire bonding pads for open or short circuits). If the initialization/hardware integrity test fails, the method 1700 may lock-out the indicator unit to prevent further use (Step 1710) and send a communication to the patient indicative of the lock-out condition, thereby advising the patient to replace the indicator unit. If the initialization/hardware integrity test succeeds, the method 1700 next determines the level of power remaining in a battery (or batteries) providing power to the indicator unit (Step 1706). If the battery power is too low to power reliably the indicator unit for at least one more treatment cycle, the indicator unit is locked out (Step 1710). If, on the other hand, there is sufficient battery power for at least one more treatment cycle, the patient is notified if the battery power is usable but low (Step 1708), and the method 1700 continues.

If the initialization test (Step 1704) and the battery power test (Step 1706) have positive outcomes, the indicator unit updates the forensic information stored on the device (Step 1714). In one embodiment, the forensic information is stored in a non-volatile memory. Examples of forensic information to be stored include one or more of the following: the results of current or previous pressure measurements; the ambient pressure, fluid pressure, and/or battery voltage at time of activation and/or initialization; the interval number, time, and/or cycle in which a product alert was generated; the number of times a warning buzzer was activated; the number of signals triggered due to a low-battery condition; the number of alerts triggered due to a blocked fluid flow, a low-fluid condition, and/or the exceeding of a time limit; the number of elapsed treatment cycles; the number of times a test button was pressed; and/or other information. In one embodiment, some or all of older forensic information is overwritten by new information; in another embodiment, old and new forensic information are maintained separately or combined to create summary information.

In one embodiment, the indicator unit enters a sleep state (Step 1712) before adapting forensic information (Step 1714) and remains in the sleep state until an external event occurs, such as the interrupt triggering of the sample timer. The sleep state may also be entered once the monitoring process 1700 completes. The sample timer may be configured to send out a trigger notification at periodic intervals, such as, for example, every 10, 15, 20, 30, or 60 minutes or more. In one embodiment, the indicator unit enters a low-power mode while in the sleep state (i.e., between sample timer trigger events), and exits the low-power mode upon leaving the sleep state.

Figure 18:
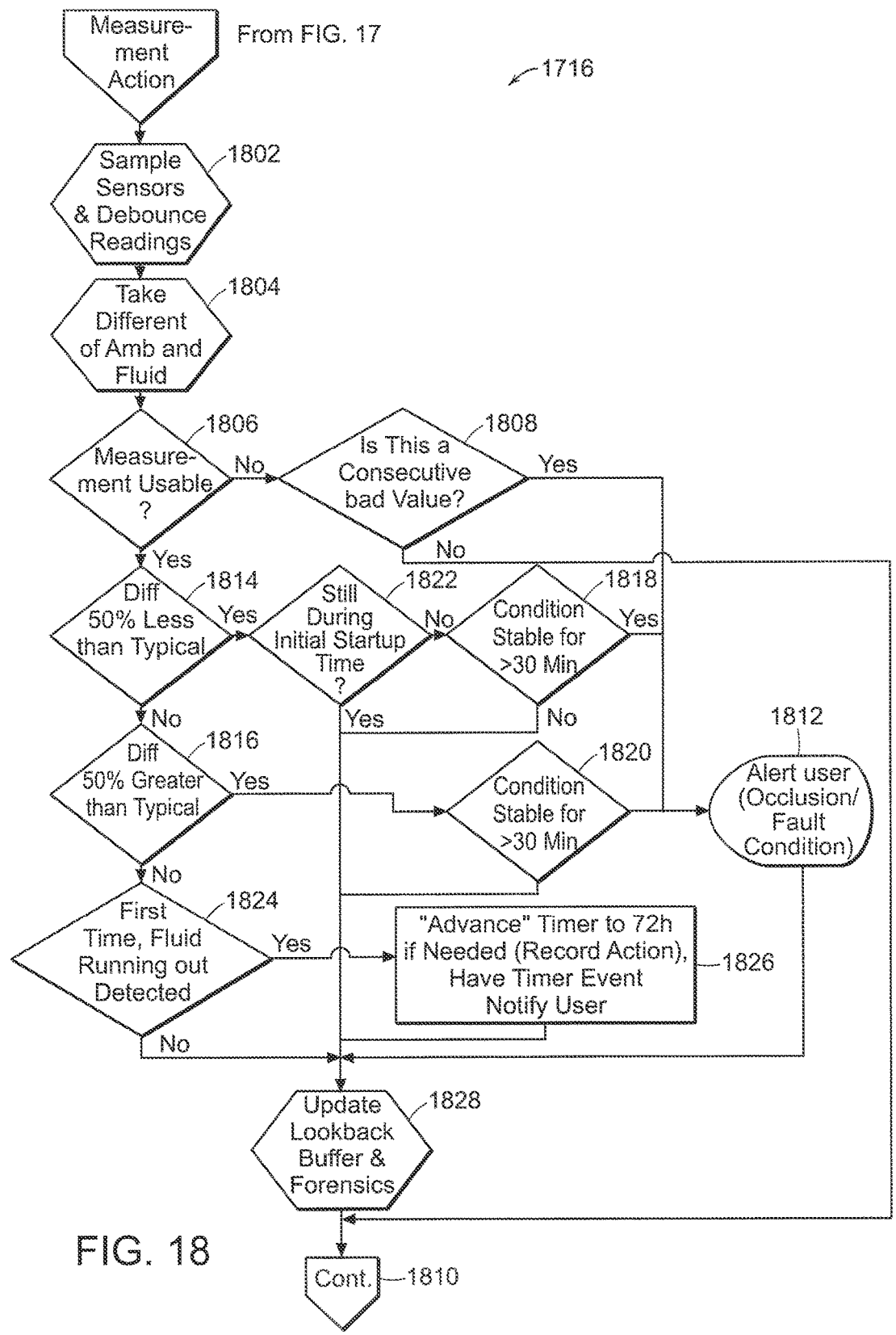
FIG. 18 is a flowchart depicting a method for measuring a fluid pressure.

Next, one or more measurement sensors are read and the results are analyzed (Step 1716), as discussed with regard to FIG. 18. Once the measurement results are obtained, an action is taken based on the length of time the indicator unit has been active (Step 1718), as discussed with regard to FIG. 19. Thereafter, the CPU may prepare the indicator unit for the next sample cycle (Step 1720). In one embodiment, the CPU sets an interrupt for the sample timer, thereby initiating its next counting cycle. The CPU may also bring the indicator unit into a low-power mode. The sample cycle then ends (Step 1722).

FIG. 18 depict one embodiment of a subroutine for reading the measurement sensors and analyzing the results (Step 1716) of the method 1700 of FIG. 17. First, a measurement signal produced by a sensor is read and, if necessary, processed to remove undesirable noise (i.e., "debounced") (Step 1802). In one embodiment, the sensor is a fluid pressure sensor and the measurement signal indicates the pressure of a medicament fluid. In another embodiment, an ambient air pressure sensor is also read to determine the ambient air pressure. If both the fluid pressure and the ambient air pressure are sensed, the difference between the pressures may be computed (Step 1804). Comparing the fluid pressure to the ambient pressure may improve the quality of the measurement results, because doing so may, for example, reduce inconsistencies in pressure reading caused by changes in altitude, as described above. The methods described herein equally apply to measurements of the fluid pressure alone.

A measurement result—which may be the fluid pressure or the difference between the fluid and ambient pressures—is analyzed to determine if it is a valid and usable measurement (Step 1806). An invalid and/or unusable measurement or "bad value" may occur because of a permanent condition, such as a hardware error in one or more of the sensors, or because of temporary condition, such as a correctly-sensed by invalid fluid pressure caused by, for example, an extreme movement of the patient and/or intense radio-frequency interference.

If a bad value is detected, previous measurements may be analyzed and compared to the current bad value to determine the nature of the bad value (Step 1808). If another bad value had recently occurred, the method may determine that the cause of the bad value is legitimate and permanent (i.e., and occlusion of the fluid flow path or a hardware fault), and accordingly notify the patient of the occlusion/fault condition (Step 1812). Alternatively, the device may also differentiate between a complete occlusion, a partial occlusion, or hardware fault condition and notify the patient accordingly. In one embodiment, the cause of the bad value, such as a fluid flow problem or a sensor malfunction, is also communicated to the patient. If, however, a usable measurement occurred in a recent prior measurement, the cause of the current bad value may be result of temporary condition. Accordingly, the measurement process exits (Step 1810) and the process is retried at the next sample timer interrupt.

If the measurement result is determined to be usable, the value of the measurement is analyzed (Steps 1814, 1816) to determine if the measurement result deviates more than a predetermined amount from a typical result. In one embodiment, the measurement result is analyzed for a deviation of 50% less than a typical value (Step 1814) or 50% greater than a typical value (Step 1816). If the measurement result deviates from the typical result by more than the predetermined amount, prior measurement results may be analyzed to determine if the amount of the deviation had been stable for more than a certain amount of time (such as, for example, 30 minutes) (Steps 1818, 1820). If so, the patient is alerted of an occlusion condition (Step 1812). The increase or decrease in pressure may be the result of an occlusion downstream or upstream from the pressure sensor, respectively.

An exception in the deviation measurement may be made during the initial startup time of the indicator unit (Step 1822). During the initial startup time (e.g., about 30 to about 60 minutes after filling of the reservoir, in one embodiment), the value of the measurement may be less than typical because, for example, the fluid pressure in the pressure sensor chamber has not yet reached its typical operating pressure. A low-pressure measurement during the initial startup time may therefore be typical of the start-up process, and the method may delay alerting the patient until after the initial startup time has elapsed. One the initial startup time has elapsed, if the error persists, the patient may then be notified.

In one embodiment, the fluid pressure in the patient attachment unit is evaluated for a sign of early depletion (Step 1824). Under normal usage, the fluid reservoir in the patient attachment unit contains a supply of fluid medicament sufficient to last for at least the unit's expected duration of use (e.g., about 72 hours). In some circumstances, though, the fluid supply may be insufficient to last for the full duration, for example where the patient uses an unexpectedly large number of bolus doses, and the indicator unit may determine that the fluid is nearing the end of its supply. In one embodiment, a low fluid condition is determined by detecting the presence of a pressure spike resulting from the last phase of contraction of an elastomer fluid reservoir. If this pressure spike is detected and distinguished from an occlusion condition, the indicator unit may advance the timer ahead to the maximum expected use time (e.g., 72 hours) (Step 1826), thereby triggering, in later steps, a patient alert signaling the dwindling fluid supply. If the sensor measurement is later run again, and a pressure spike is again detected, the previously-advanced timer value is not disturbed. In one embodiment, the peak pressure of the pressure spike is about 15% to about 20% greater than a typical baseline steady state pressure in the basal circuit. Other peak pressures may also be considered. For example, a typical pressure of the fluid may be 400 bar. During the initial startup time, the fluid pressure starts at 0 bar and increases to 400 bar, though no low-pressure alert is generated. Once the initial startup time has elapsed, if the pressure is less than 200 bar or greater than 600 bar, the occlusion test steps 1814, 1816 detect an occlusion condition. If there is a pressure spike of approximately 460-480 bar, the early depletion step 1824 detects a low fluid condition.

Before the sensor measurement completes, one or more items of information determined during the course of the sensor measurement (Step 1828) may be stored in the non-volatile memory, as described above. In one embodiment, the information is stored in a non-volatile forensic buffer. In another embodiment, one or both of the pressures determined in the measurement step are stored in a lookback pressure buffer, thereby preserving the pressure(s) for use in, for example, future sensor measurement comparisons to evaluate data trends or for other purposes.

Figure 19:
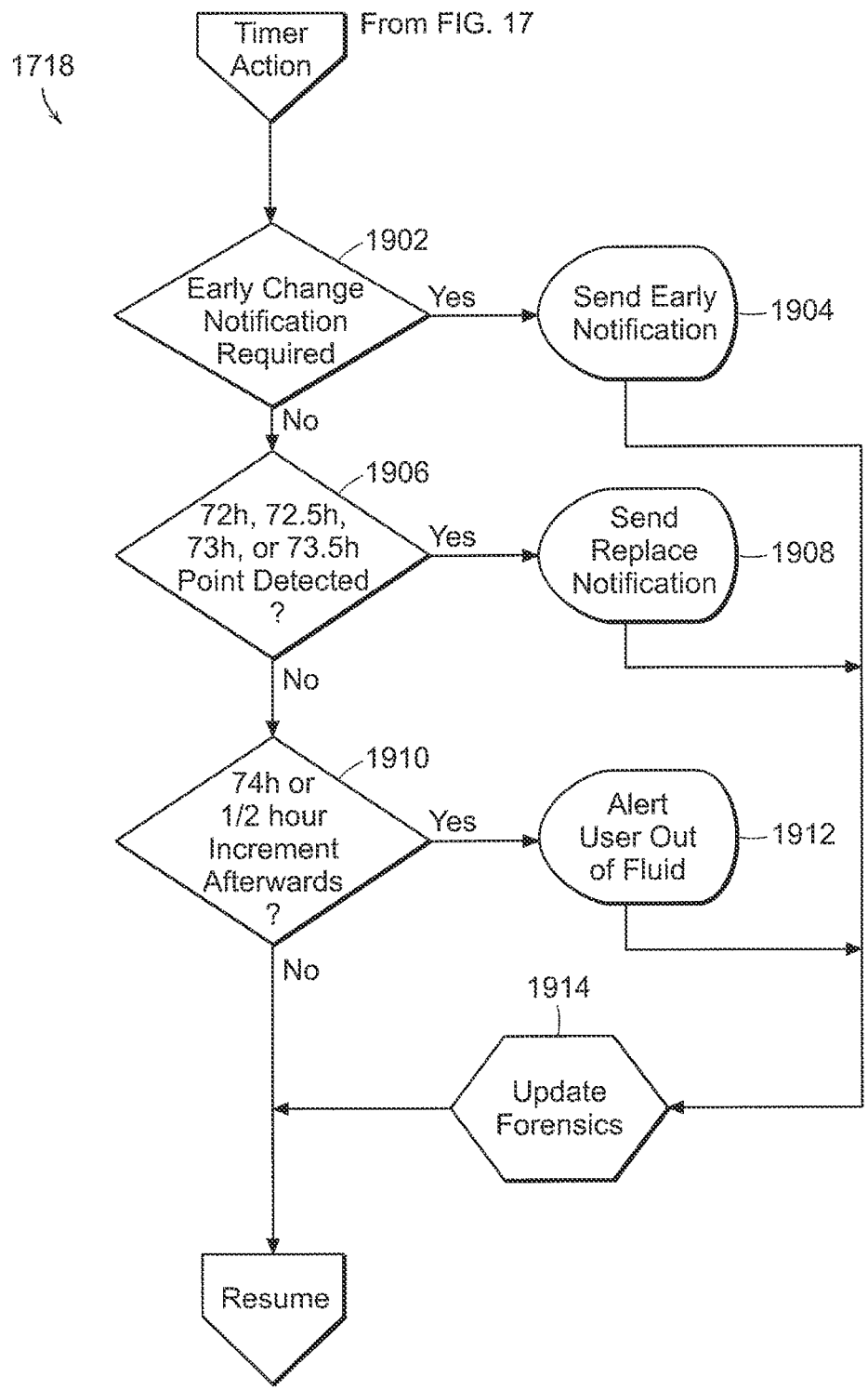
FIG. 19 is a flowchart depicting a method for notifying a patient of a timer event.

FIG. 19 depicts one embodiment of a subroutine for reading the timer and taking an appropriate action (Step 1718) of the method 1700 of FIG. 17. In this subroutine, the value of the timer may be compared against one or more threshold times, and the patient is alerted if a threshold has been reached. For example, the value of the timer is compared against an early change notification time (e.g., 48 hours) (Step 1902). If the early change notification time has elapsed, a notification is sent to warn the patient that the patient attachment unit may soon require replacement (Step 1904). In one embodiment, if the patient presses a test button before the early change notification time has elapsed, the indicator unit sends either no response or a response indicating that the unit is operating normally. If, however, the patient presses the test button after the early change notification time has elapsed, the indicator unit may send a warning signal, such as a vibration, to inform the patient that the patient attachment unit may soon require replacement.

The timer value is also compared to the maximum expected time of use (e.g., about 72 hours) (Step 1906). If the timer exceeds the maximum expected time of use, a "Replace" notification is sent to the patient (Step 1908) instructing the patient to replace the patient attachment unit. In one embodiment, further "Replace" notification are sent to the patient at later intervals of time, for example, at about 72.5 hours, about 73 hours, and at about 73.5 hours, urging replacement of the patient attachment unit. The "Replace" notification can be more urgent (e.g., louder, stronger, longer, etc.) as additional time elapses.

Once the value of the timer passes a second threshold (Step 1910), however, an out-of-fluid alert is sent to the patient (Step 1912). The second threshold may be a predetermined time at which the fluid reservoir will run out of fluid. In one embodiment, the out-of-fluid alert is repeatedly sent to the patient, for example, every thirty minutes.

After each notification and/or alert is sent to the patient, relevant forensic information may be recorded (Step 1914). The forensic information may include the type of timer action triggered, the type of alert sent, the number of times the bolus button is pressed and/or the total number of actions and alerts. Patient acknowledgement of receipt of an alert and/or notification by, for example, pressing a response button, may also be recorded.

Figure 20:
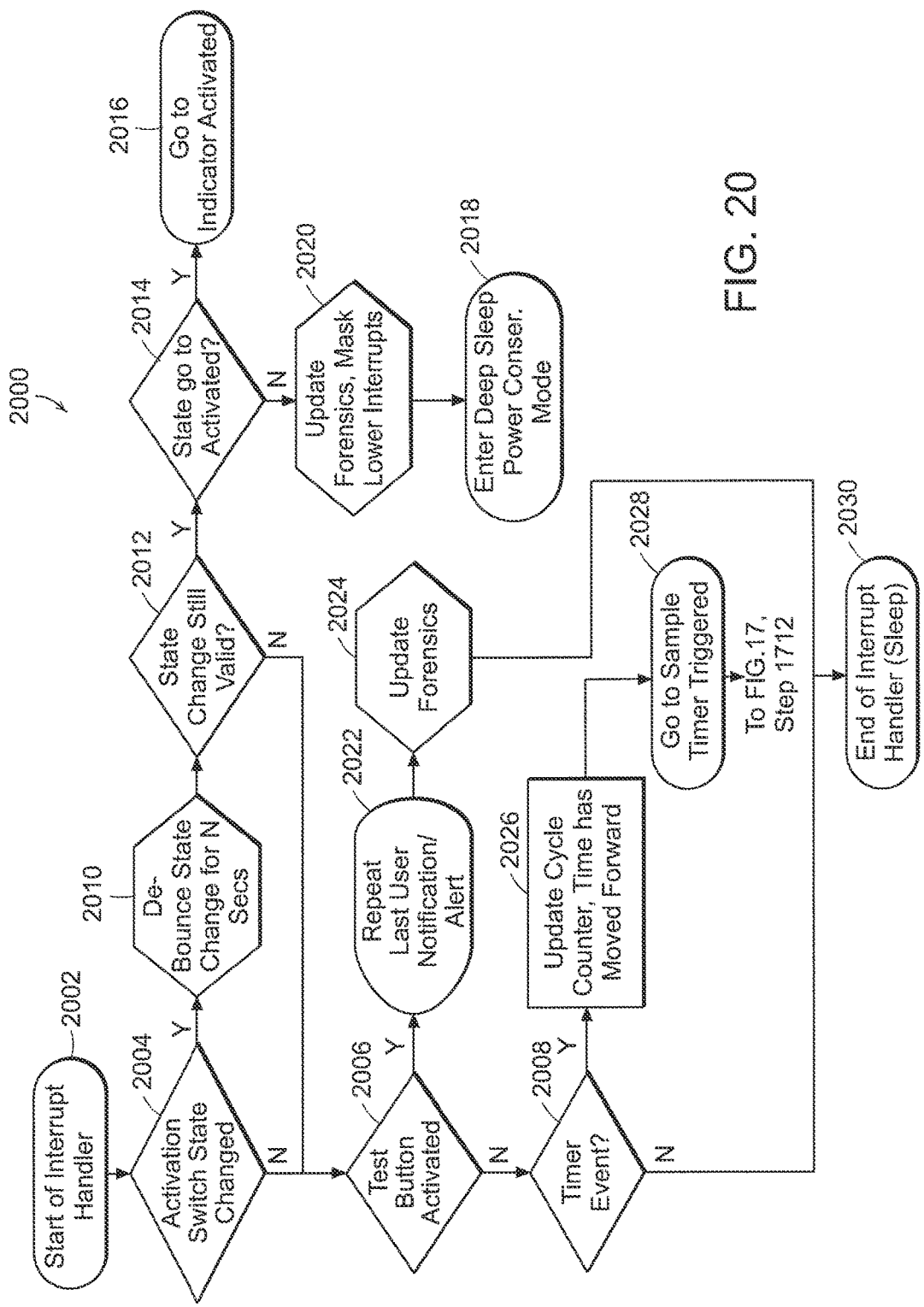
FIG. 20 is a flowchart depicting a method for handing interrupts.

The indicator unit may interact with external event, such as switch toggles, button presses, and timer events, by means of an interrupt handler. A flow chart illustrating one embodiment of an interrupt handler process 2000 is shown in FIG. 20. Proceeding from an interrupt event (Step 2002), the interrupt handler process 200 illustrates the handling of three categories of events—a switch event (Step 2004), a button event (Step 2006), and a timer event (Step 2008)—but other, similar categories of events are contemplated and within the scope of the invention.

The switch event (Step 2204) detects a change in the state of an activation switch on the indicator unit. The signal generated by the activation switch is debounced (Steps 2010, 2012), wherein the signal is monitored for consistency over N seconds until a clean change in the state of the activation switch is detected. The new state of the activation switch is evaluated (Step 2014). If the new state is activated or "on," the indicator unit may be powered on (Step 2016) by, for example, transferring control to the first step of the main loop 1700, starting at step 1702, as depicted in FIG. 17. In one embodiment, certain interrupts are masked to prevent the indicator unit from waking up when certain events occur (Step 2020). For example, in sleep mode, the indicator unit may ignore presses of a test button, but may wake up front sleep mode when the activation switch toggles. Forensic information (such as the time of entry into the sleep mode, the calculated fluid reservoir capacity, number of times a bolus button was pressed, and/or the battery power available) may be written to the non-volatile memory (step 2020). If the new state is deactivated or "off," the indicator unit may be placed into a power-conserving "deep sleep" mode (Step 2018), to conserve battery power. This mode may be useful for shipment or storage of the patient attachment unit.

The indicator unit may include a test or "indicator" button permitting a patient to check the status of the unit upon actuation. Additionally, the indicator button may be used to silence a notification currently being delivered. An interrupt created by the actuation of the button is detected (Step 2006) and the last notification and/or alert sent to the patient is determined (by, for example, reading past forensic information from the non-volatile memory) and re-sent (step 2022). In one embodiment, the indicator unit performs a new pressure measurement in response to the pressing of the test button, and sends a notification based on the new measurement. The sending of the repeated notification and/or the new test result may be saved to the non-volatile memory (Step 2024). In other embodiments, different patterns of test button presses are detected and produce different types of interrupts. The indicator unit may include additional buttons to perform different functions.

The expiration of the sample timer, which may occur at regular intervals, about every 5, 10, 15, 20, 25, or 30 minutes, for example, may trigger a timer event (Step 2008). At each sample timer event, a cycle counter may be incremented (Step 2026), and the main sample loop 1700 (depicted in FIG. 17) may be launched (Step 2028), starting at Step 1712. The interrupt handler routine ends regardless of the type of interrupt (Step 2030) and enters a sleep state awaiting the next interrupt.

At each expiration of the sample timer, the total time of use of the indicator unit may be determined by multiplying the current cycle counter value by the sample time expiration value. For example, if the sample timer expires every 30 minutes and the value of the cycle counter is ten, the total time of use is 300 minutes or 5 hours, the product of the sample time period and the number of cycles. Thus, steps that require the total time of use, for example, timer Steps 1902, 1906, may determine the total time of use from the sample rate and cycle counter.

Figure 21:
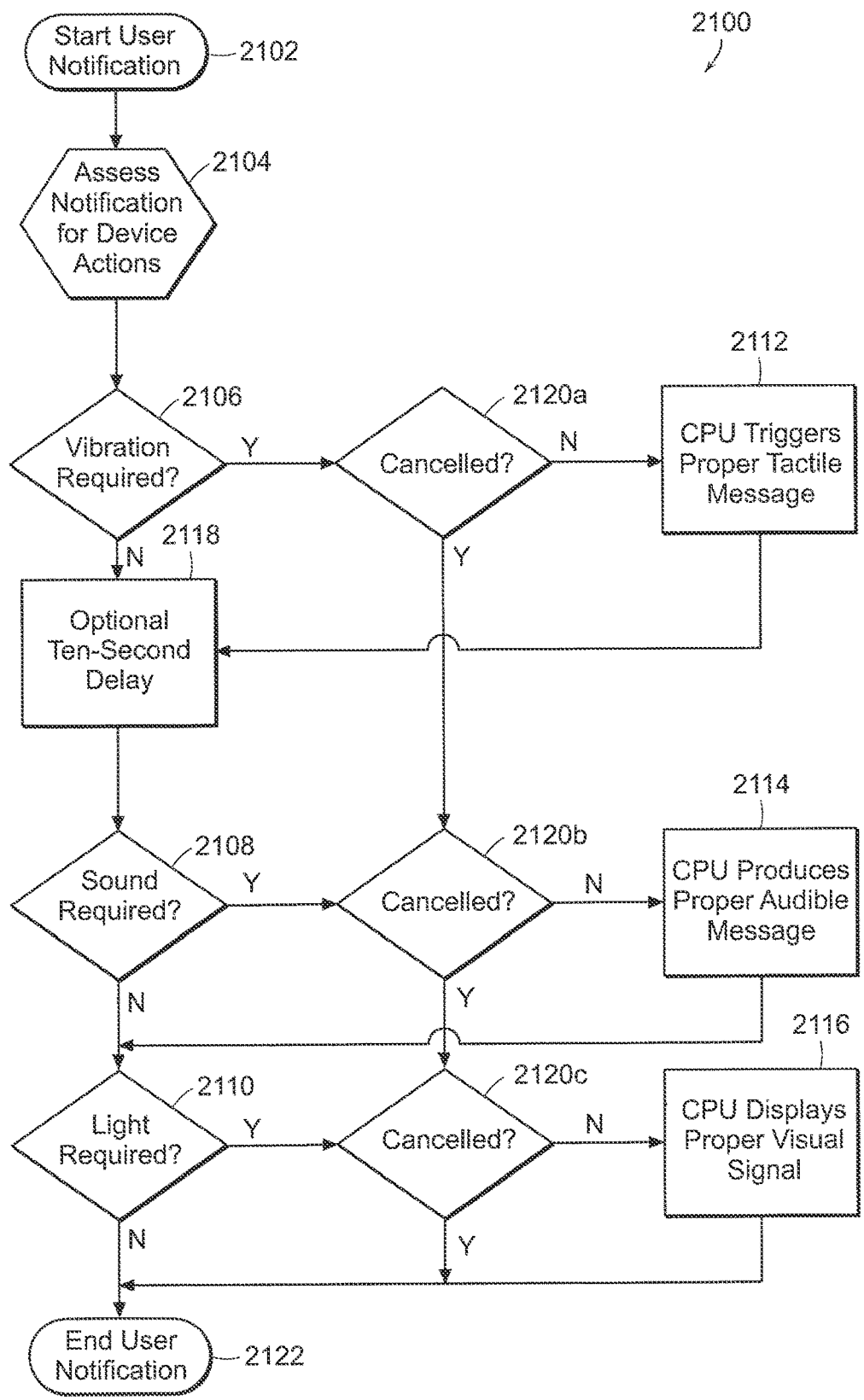
FIG. 21 is a flowchart depicting a method for providing feedback to a patient.

FIG. 21 depicts one embodiment of a method 2100 for determining the type of Patient notification required. Different types of notifications or alerts may be communicated to the patient by different means, depending on the type and/or urgency of the notification or alert. The medicine delivery device described herein generally utilized discreet notifications to alert a patient to particular conditions, without unnecessarily alerting nearby persons to the patient's use of the device. For example, an alert of notification may trigger a tactile message (i.e., a vibration) at first but, if the patient fails to respond to or is unable to detect the tactile message, the type of notifications or alert may escalate to more observable types (e.g., sound, lights, etc.) alone or in combination. Frequency and magnitude of notification or alert can also be escalated. The process starts (Step 2102) and evaluates the source of the patient notification request (Step 2104). Less urgent notifications or alerts may require only a brief notification, while more urgent notifications or alerts may require more extensive notifications. The notifications or alerts may vary in type (e.g., light-based for minor events, sound-based for intermediate events, and vibration-based for important events) and degree (e.g., brighter or dimmer lights, different colors of lights, louder or softer sounds, and/or stronger or weaker vibrations). For example, the patient may be notified of a successful pressure test with a green light and of a low-fluid condition with vibration. In one embodiment, two or more types of alerts are combined in the same notification. The patient may specify a preferred type of notification (e.g., vibration-based for hearing-impaired patients or sound-based for visually-impaired patients).

Once the type of notification is assessed (Step 2104), the notification requirements are evaluated to determine if vibration, sound and/or light is required (Steps 2106, 2108, 2110). The CPU produces the corresponding vibration, sound, and/or light notifications in response (Steps 2112, 2114, 2116). A discretion delay may be inserted between a first discreet notification and a second over notification (Step 2118) to allow the patient to cancel the notification or alert once the discreet notification is received. In one embodiment, a tactile message (e.g., a vibration) is first sent and the patient is given a ten-second window to cancel the notification by, for example, pressing the test button (Step 2120*a*). If the test button is pressed, the patient thereby acknowledges receipt of the notification and no further notifications are sent. If, however, the patient does not press the test button, the notification may escalate to sound and/or light-based messages. In another embodiment, a light-based message is sent first, and a tactile- and/or sound-based message is sent after a delay. The patient notification may be cancelled during escalated notifications (Steps 2120*b*, 2120*c*), as well as during the first, discreet notification (Step 2120*a*).

In one embodiment, the patient notification conveys information regarding the notification type. For example, a green light may signify an "OK" state, a yellow light a "warning" state, and a red light an "error" state. In one embodiment, a sound-based notification includes two or more tones. The tones may be arranged, for example, at a high pitch, with an increasing or rising frequency, and/or in accordance with a major scale to convey an "OK" state. On the other hand, the tones may be arranged at a low pitch, with decreasing frequency, and/or in accordance with a minor scale to convey a warning or error state. Tones or sounds may include those generally recognized by a human as having positive or negative associations. The patient notification process ends when the appropriate notifications have been sent (Step 2122).

While there have been described herein what are to be considered exemplary and preferred embodiments of the present invention, other modifications of the invention will become apparent to those skilled in the art from the teachings herein without departing from the spirit or essential characteristics thereof. The present embodiments are therefore to be considered in all respects as illustrative and not restrictive. The particular methods of manufacture, geometries, and methods of operation disclosed herein are exemplary in nature and are not to be considered limiting. It is therefore desired to be secured in the appended claims all such modifications as fall within the spirit and scope of the invention. Accordingly, what is desired to be secured by Letters Patent is the invention as defined and differential in the following claims, and all equivalents.

What is claimed is:

1. A system for monitoring a fluid medicament delivery device, the system comprising:
    a patient attachment unit comprising a pressure sensor chamber disposed along a basal flow path, wherein the pressure sensor chamber comprises a sensor membrane; and
    an indicator unit configured to be detachably coupled to the patient attachment unit, wherein the indicator unit comprises a pressure sensor in communication with the pressure sensor chamber, wherein the indicator unit comprises a well in which the pressure sensor is disposed, and wherein the well is filled with a gel to form a meniscus.

2. The system of claim 1, wherein the well comprises a raised lip.

3. The system of claim 2, wherein the raised lip is configured to abut a mounting platform of the patient attachment unit.

4. The system of claim 1, wherein the meniscus and the sensor membrane abut each other.

5. The system of claim 4, wherein deflections in the sensor membrane are configured to apply pressure to the meniscus of the gel, which transmits the pressure to the pressure sensor.

6. The system of claim 1, further comprising an ambient air channel formed between the patient attachment unit and the indicator unit.

7. The system of claim 6, further comprising a flexible pressure equalizing membrane disposed in the patient attachment unit, wherein the flexible pressure equalizing membrane is in communication with the ambient air channel.

8. The system of claim 6, further comprising a second pressure sensor disposed within the indicator unit.

9. The system of claim 8, wherein the indicator unit further comprises a second well in which the second pressure sensor is disposed.

10. The system of claim 9, wherein the second well is filled with a gel to form a meniscus, which is in communication with the ambient air channel.

11. A system for monitoring a fluid medicament delivery device, the system comprising:
a patient attachment unit comprising a mounting platform and a pressure sensor chamber disposed along a basal flow path, wherein the pressure sensor chamber comprises a sensor membrane; and
an indicator unit configured to be detachably coupled to the patient attachment unit, wherein the indicator unit comprises a pressure sensor disposed in a well having a raised lip, wherein the well is filled with a gel to form a meniscus, and wherein the pressure sensor is in communication with the pressure sensor chamber,
wherein the raised lip is configured to abut the mounting platform to form an ambient air channel between the patient attachment unit and the indicator unit.

12. The system of claim 11, wherein the meniscus and the sensor membrane abut each other.

13. The system of claim 12, wherein deflections in the sensor membrane are configured to apply pressure to the meniscus of the gel, which transmits the pressure to the pressure sensor.

14. The system of claim 11, further comprising a flexible pressure equalizing membrane disposed in the patient attachment unit, wherein the flexible pressure equalizing membrane is in communication with the ambient air channel.

15. The system of claim 11, further comprising a second pressure sensor disposed within the indicator unit.

16. The system of claim 15, wherein the indicator unit further comprises a second well in which the second pressure sensor is disposed, wherein the second well is filled with a gel to form a meniscus that is in communication with the ambient air channel.

17. A method for monitoring a fluid medicament delivery device, the method comprising:
providing a patient attachment unit comprising a pressure sensor chamber disposed along a basal flow path;
providing an indicator unit configured to be detachably coupled to the patient attachment unit, wherein the indicator unit comprises a pressure sensor in communication with the pressure sensor chamber, wherein the indicator unit comprises a well in which the pressure sensor is disposed, and wherein the well is filled with a gel to form a meniscus; and
determining a pressure condition in the basal flow path.

18. A system for monitoring a fluid medicament delivery device, the system comprising:
a patient attachment unit comprising a pressure sensor chamber disposed along a basal flow path, wherein the pressure sensor chamber comprises a sensor membrane; and
an indicator unit configured to be detachably coupled to the patient attachment unit, wherein the indicator unit comprises a pressure sensor in communication with the pressure sensor chamber;
an ambient air channel formed between the patient attachment unit and the indicator unit;
a second pressure sensor disposed within the indicator unit, wherein the indicator unit comprises a second well in which the second pressure sensor is disposed.

* * * * *